(12) United States Patent
Avrahamson

(10) Patent No.: US 10,478,115 B2
(45) Date of Patent: Nov. 19, 2019

(54) HANDHELD HOME MONITORING SENSORS NETWORK DEVICE

(75) Inventor: Dan Avrahamson, Birkerød (DE)

(73) Assignee: SpiroFriend Technology ApS, Copenhagen Ø (DK)

(*) Notice: Subject to any disclaimer, the term of this patent is extended or adjusted under 35 U.S.C. 154(b) by 689 days.

(21) Appl. No.: 11/576,624

(22) PCT Filed: Oct. 4, 2005

(86) PCT No.: PCT/DK2005/000635
§ 371 (c)(1),
(2), (4) Date: May 1, 2007

(87) PCT Pub. No.: WO2006/037331
PCT Pub. Date: Apr. 13, 2006

(65) Prior Publication Data
US 2008/0281220 A1    Nov. 13, 2008

Related U.S. Application Data

(60) Provisional application No. 60/615,813, filed on Oct. 4, 2004.

(51) Int. Cl.
*A61B 5/097* (2006.01)
*A61B 5/00* (2006.01)
(Continued)

(52) U.S. Cl.
CPC ............ *A61B 5/411* (2013.01); *A61B 5/0002* (2013.01); *A61B 5/087* (2013.01); *A61B 5/097* (2013.01);
(Continued)

(58) Field of Classification Search
USPC .......................................... 600/529–543, 586
See application file for complete search history.

(56) References Cited

U.S. PATENT DOCUMENTS 5,676,154 A * 10/1997 Pettersson ..................... 600/532
5,797,852 A *  8/1998 Karakasoglu et al. ....... 600/529
(Continued)

FOREIGN PATENT DOCUMENTS

| EP | 1391178 A | 2/2004 |
|----|-----------|--------|
| WO | WO-00/50890 A | 8/2000 |

(Continued)

OTHER PUBLICATIONS

"End-tidal". The Free Dictionary Apr. 3, 2015, medical dictionary, http://medical-dictionary.thefreedictionary.com/end-tidal.*

*Primary Examiner* — Michael R Bloch
(74) *Attorney, Agent, or Firm* — Julie K. Staple; Dinsmore & Shohl LLP

(57) ABSTRACT

Light weight personal handheld home monitoring and managing device, which includes a Sound Sensor network/array of Sound Sensor networks combined with an Artificial Neural Network (ANN) and a build in system and methods, making this device an intelligent and portable apparatus to address specific health issues. The combined apparatus is used for managing and/or guidance and/or diagnosing and/or controlling and managing purposes. This present version of the apparatus will address pulmonary disorders and diseases or similar ailments.

15 Claims, 40 Drawing Sheets

(51) Int. Cl.
    *A61B 5/087*     (2006.01)
    *A61B 7/00*     (2006.01)
    *A61B 5/0205*     (2006.01)

(52) U.S. Cl.
    CPC ............ *A61B 5/7267* (2013.01); *A61B 7/003* (2013.01); *A61B 5/0205* (2013.01)

(56) References Cited

U.S. PATENT DOCUMENTS

| | | | |
|---|---|---|---|
| 6,213,955 B1 | 4/2001 | Karakasoglu et al. | |
| 6,241,683 B1 * | 6/2001 | Macklem et al. | 600/529 |
| 6,402,697 B1 * | 6/2002 | Calkins et al. | 600/532 |
| 6,443,907 B1 * | 9/2002 | Mansy et al. | 600/529 |
| 6,565,517 B1 * | 5/2003 | Rasmussen | 600/529 |
| 6,852,084 B1 * | 2/2005 | Boesen | 600/528 |
| 6,954,702 B2 * | 10/2005 | Pierry et al. | 702/22 |
| 2002/0165462 A1 * | 11/2002 | Westbrook et al. | 600/529 |
| 2003/0008407 A1 * | 1/2003 | Fu | 436/161 |
| 2003/0208133 A1 * | 11/2003 | Mault | 600/532 |
| 2004/0081587 A1 * | 4/2004 | Melker et al. | 422/84 |
| 2004/0127808 A1 * | 7/2004 | Vaughan et al. | 600/532 |
| 2004/0162500 A1 * | 8/2004 | Kline | A61B 5/097 600/532 |
| 2004/0186390 A1 * | 9/2004 | Ross et al. | 600/532 |
| 2005/0192508 A1 * | 9/2005 | Lange et al. | 600/534 |

FOREIGN PATENT DOCUMENTS

| | | |
|---|---|---|
| WO | WO 0193743 A2 * | 12/2001 |
| WO | WO-03/022149 A | 3/2003 |
| WO | WO-2004058064 A2 | 7/2004 |

\* cited by examiner

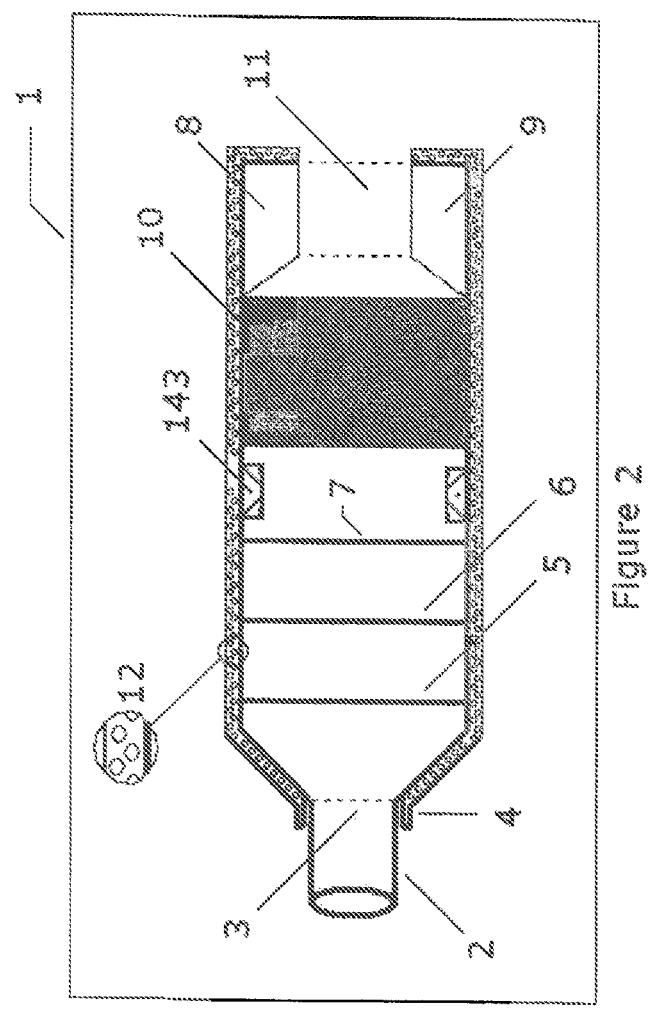

| Date and time | Parameter |
|---|---|
| 07.10.2003 ; 11:05 PM | 64.4567 |
| ... | ... |

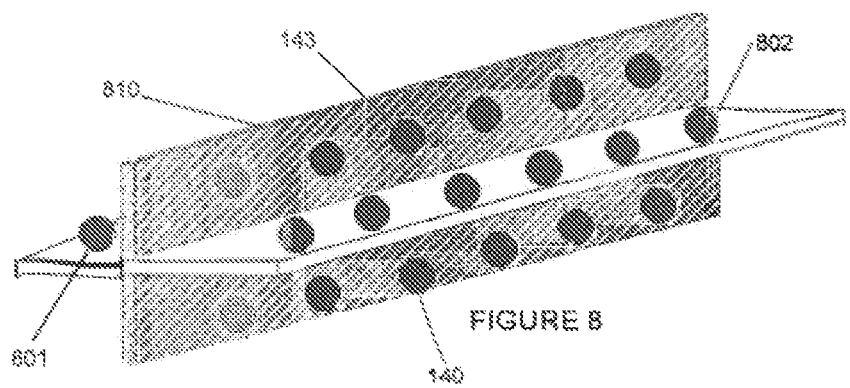

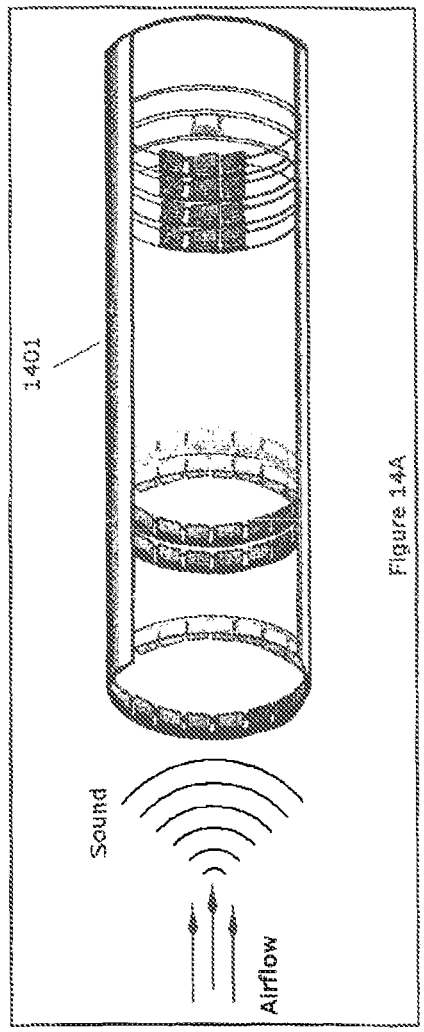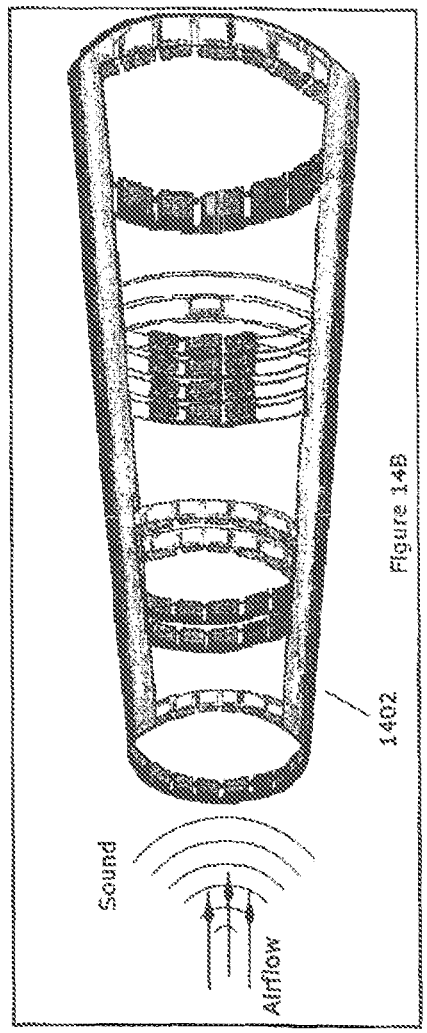

HANDHELD HOME MONITORING SENSORS NETWORK DEVICE

The description is made for the purpose of illustrating the general principles of the invention and should not be taken in a limiting sense.

FIELD OF THE INVENTION

The invention relates to a light weight personal handheld home monitoring and managing device, which includes a Sound Sensor network/array of Sound Sensor networks combined with an Artificial Neural Network (ANN) and a built-in system and methods, making this device an intelligent and portable apparatus to address specific health issues. The combined apparatus is used for imaging and/or guidance and/or diagnosing and/or controlling and managing purposes. The present version of the apparatus will address pulmonary disorders and diseases or similar ailments.

BACKGROUND OF THE INVENTION

Asthma is one of the most common chronic, pulmonary diseases in the world, found in both adults and children. In all parts of the world asthma is a fast growing disease. The prevalence of asthma increases as communities adopt western lifestyles and become urbanized.

According to the latest report from the Global Initiative for Asthma (GINA) it is estimated that as many as 300 million people of all ages and all ethnic backgrounds suffer from asthma, and that the burden of this disease to governments, health care systems, families, and users is increasing worldwide.

It is also estimated, that there may be an additional 100 million persons suffering from asthma by year 2025.

Asthma is considered a chronic pulmonary disease. As of today no cure exists. However, stabilizing the disease with the right medication at the right time may preserve the life quality for human beings.

Pre and post diagnosis and home monitoring of the pulmonary function is instituted by the general practitioner accordingly. This includes repeated daily measurements of the pulmonary function and logging of data and symptoms, which is considered essential for the general practitioner to make a precise diagnosis, choose the right treatment, and decide on the medication.

Diagnosed asthmatics are very dependent upon an acceptable control of their disease and the management of the day-to-day adjustment of their medication.

Well-known problems with asthmatic home monitoring today are users lack of compliance, wrong use and lack of precision in the devices used for the home measurements, causing reduced life quality for the user when asthma is not stabilized.

This invention reduces errors in home measurements. The device uses a network of Sound Sensors and a self-correlating system in an Artificial Neural Network to analyze the collected physiological data originating from the behavior pattern of a specific user. The device compares these data with data previously collected and stored by the device about the same user and/or loaded calibrated information stored about the user and/or loaded reference information based upon information from a background population. This generates a unique and accurate picture of the user's disease based on the behavior pattern.

The recorded data is stored in the devices storage unit continuously with a set of date and time registration details.

To shorten learning time for artificial neural network unit, it is possible to upload user data to the device. Pre-measured data can also be uploaded to the device.

The interpretation of behavior pattern is improved by logging of the user condition and making suggestions to support the self-control of medicine to take.

This invention also deals with a cooperative calculation approach for using artificial neural network ensembles and applies multi objective optimization.

Cooperative calculation approach is a recent paradigm in evolutionary computation that allows through a learning process to model the lungs sound and the acoustic of respiratory passage and its cooperative environments for a specific user in relation to itself. Although processing algorithms that make the device able to handle with its artificial neural network and with a sufficient number of neurons in the hidden layer would suffice to solve user diseases behavior pattern and indicate or alarm the appearance of a given condition for the user for example an asthmatic attack.

SUMMARY OF THE INVENTION

The invention relates to a light weight personal handheld home monitoring device, with an in build network of Sound Sensors, artificial neural network system, intelligence and portable device, system and method addressing a specific health issue.

The system and method is used for imaging and/or guidance and/or diagnosing and/or controlling purposes. The main aspect of present version relates to normal pulmonary health care, disorder and diseases or similar health conditions or ailments.

The invention relates to a method and system for specific recognition of lungs function conditions, especially the presence of specific sound(s) that can be related to a given specific lung function condition with the user himself as reference. That means an easy accurate method to learn and recognize a given user disease behavior pattern and accuracy condition and compare with user.

For this purpose, a special network of sound sensors is introduced into the breathing apparatus. Preprogrammed sounds provide information about sound signatures. When certain conditions are detected, actions such as activating an alarm signal are carried out. A simultaneous control of the signal by a user is made possible by representing the signals on a display or by the output thereof on loud speaker/headphones or the like.

The device, system and method are specially designed for improvements in the early diagnosis and prevention of Pulmonary Function Disorder and Diseases (PFDD), in particular Asthma and COPD.

The device is generally capable of being used as an electronic journal, data acquisition, storage of measurements, medicine optimizer, storage of typed input data and user health and diseases pattern behavior. Using the device in the ongoing measurement, the devise will after a period analyze the stored measurements and set some indication FLAGS that the general practitioner can use in his overall diagnosis, treatment and choice of medication.

The device is able to establish communication to a data processor through a wire or wireless connection (for example USB, Bluetooth, infrared etc.) and transmit and receive data/information to and from the data processor via a software interface. The measured data or information can also be shown as real time curves and plots.

As the device is flexible in its design, it is independent of the type of disease to acquire data/information about. This means that the equipment can be adapted for several types of measurements, just by changing the loaded software with respect to the used Sound Sensor Networks.

For example a system and method for testing and recording the peak expiratory flow rate (PEFR), forced expiratory volume (FEV1), (FEV6) and forced volume capacity (FVC) of an asthmatic user, comprises (I) prompting the user to cause the sensing of the expiratory and/or inhalation flow rate, (II) sensing the expiratory and/or inhalation flow rate of the user and (III) generating a signal representative of this biological condition, (IV) processing the signal to generate biological data representative of the biological condition, (V) generating date and time stamp data representative to the date and time when the biological condition was sensed, (VI) storing the biological data and the date and time data, and (VII) retrieving the stored biological data together with the time stamp data (VIII) analyzing the stored information using an artificial intelligence analytic method, (IX) displaying the result of the analysis, (X) storing the result for later reference and analysis.

Methods for using the Sound Sensor Network device, system and methods for making the sensor device also are disclosed.

BRIEF DESCRIPTION OF THE DRAWINGS

FIG. 1A-1 is an example of the physical dimensions of the main device.

FIG. 1A-210 is a right ear device.

FIG. 1A-211 is a left ear device.

FIG. 1A-555 is a wireless bidirectional interconnection between the left and/or right ear devices and/or main device.

FIG. 1B-110 is a main device block diagram overview.

FIG. 1B-200 is a sound sensor network as shown in FIG. 3,4.

FIG. 1B-240 is an analog to digital converter.

FIG. 1B-245 is a signal analysis process connected to the data bus.

FIG. 1B-260 is a random accessible memory connected to a data bus.

FIG. 1B-261 is a read only memory storing connected to the data bus.

FIG. 1B-262 is a data bus connecting the various blocks.

FIG. 1B-265 is a mass storage component for the captured sensor data.

FIG. 1B-270 is a data processing unit.

FIG. 1B-280 is a user interface.

FIG. 1B-285 is a data input monitor and key pad.

FIG. 1B-295 is a software program that is developed for the device.

FIG. 1B-300 are other sensors connected to the ADC.

FIG. 1B-400 is an artificial neural network.

FIG. 1B-500 is a power supply of the device.

FIG. 1B-510 is an external interface wireless and/or wired link.

FIG. 1C-199 illustrates an amplifier, which is matched to a sensor.

FIG. 2 shows an example of a detailed cross sectional view of the front end and the back end of the Sound Sensor network device.

FIG. 2-2 Exchangeable mouthpiece

FIG. 2-3 Exchangeable micro filter to capture moisture, dust, bacteria and similar particles.

FIG. 2-4 Socket to keep mouthpiece and its filter and changeable mouthpiece.

FIG. 2-5 Sound Sensor Network (SSN).

FIG. 2-5+6+7 Array of Sound Sensor Networks (ASSN).

FIG. 2-8+9 Hardware and software such as Artificial Intelligence (AI), memory, data processor like device, add on memories, other electronics accessories and rechargeable battery.

FIG. 2-10 Changeable medico technique module.

FIG. 2-11 Bidirectional Air Flow Detector (BAFD), Flow Meter (FM), breathing frequent counter and output ventilation port.

FIG. 2-12 Sound damping material, to minimize common mode sound and noise.

FIG. 2-143 Sound sensors for elimination of common mode sound and noise

FIG. 3 shows cross-sectional views of the sound sensor network built into the airflow tube. This view is referenced to the cross-sectional view as illustrated in FIG. 2.

FIG. 3-5. The first level of Sound Sensors

FIG. 3-6. The second level of Sound Sensors

FIG. 3-7. The third level of Sound Sensors.

FIG. 3-12. Sound damping material, to minimize common mode sound and noise.

FIG. 3-13. Block of Sound Sensors to eliminate ambient and common mode sound and noise.

FIG. 3-140 A sound sensor placed in the first network layer.

FIG. 3-141 A sound sensor placed in the second network layer.

FIG. 3-142 The center sound sensor in the third layer.

FIG. 3-143 A sound sensor to eliminate ambient and common mode sound and noise.

FIG. 4 provides a front view of the sound sensor network as seen from the front end of the airflow tube as illustrated in FIG. 2.

FIG. 4-140 Sound sensor placed in the first network layer.

FIG. 4-141 Sound sensor placed in the second network layer

FIG. 4-142 The center sound sensor in the third layer.

FIG. 4-143 Sound sensor to eliminate ambient and common mode sound and noise.

FIG. 4-5 First level of Sound Sensors.

FIG. 4-6 Second level of Sound Sensor

FIG. 4-7 Third level of Sound Sensors.

FIG. 4-13 Block of Sound Sensors to eliminate ambient and common mode sound and noise.

FIG. 5A-220 Sound and/or Temperature and/or Pressure sensors.

FIG. 5A-222 Sound and/or Temperature and/or Pressure sensors.

FIG. 5A-224 Temperature and/or Pressure and/or Moisture and/or Sound Sensors.

FIG. 5B Possible placement of the ear device on the body.

FIG. 6 Example of a data set.

FIG. 8 shows an alternative implementation of a Sound Sensor Network.

FIG. 10 shows an example of a software implementation.

FIG. 11 an example of a process going from a data input set to condition prediction and ANN classification.

FIG. 12 An example of an activation plan and an ANN output data set.

FIG. 13 An ANN and the Sound Sensor network groups G1 to G6.

FIGS. 14A and 14B show an illustration of an alternative to the Sound Sensor in FIG. 2.

DETAILED DESCRIPTION OF THE INVENTION

Figure 1A:
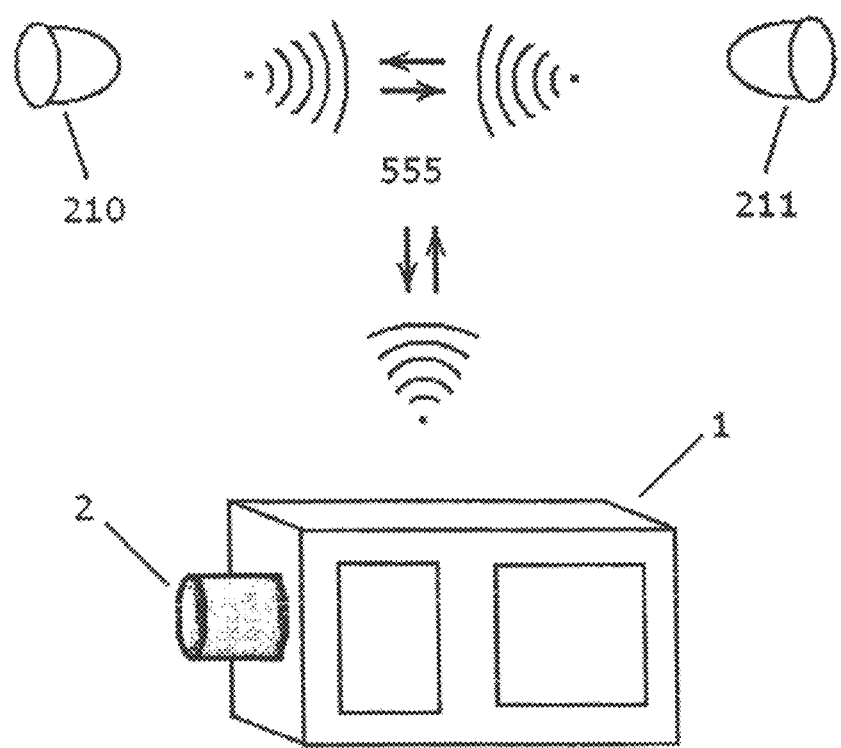
FIG. 1A shows the main device with two external ear devices.

The term "device" or "the device" or "main device" refers generally to the mother device.

The expression "a given" medical term or "a given" technical term means/refers to a given mathematical calculation, a given algorithm, a given technique, a given principal a given process, a given progress, a given condition, a given diseases and/or two or any combination of them.

The term "user" refers to a patient, person, adult, children, athlete and/or living organism as well as healthy and ailing person.

The term "Doctor" refers to a medical Doctor, medical specialist, Physician, Hospital, medical clinic or the like, i.e. a person able to understand, analyze, treat and make decision based on a given medical circumstance, condition, disease, or the like.

The term "sound" refers to a respiratory sound generated by a human or a living organism, which can be generated in the process of normal respiratory process by for example a regular healthy user or a sportsman, or abnormal respiratory process, caused by asthma, bronchitis, allergy, COPD (Chronic Obstructive Pulmonary Disease), physical lung reduction or other lung functionality disturbances. The sound can be generated during sleep, under narcosis, coma or consciousness. By "sound" is meant wheezing, crackles, snores, striders and the like.

The term "Sound Sensor Network" or "SSN" refers to a network of few or several sound sensors, that are connected in a network, which may consist of parallel, serial, differential, summative, subtractive, organized in a matrix, or combinations hereof. For example the sound sensors may in case of noise compensation collect the environmental or ambient sounds as a common mode signals and the sound information as differential signals According to those principles, some of SSN can be coupled differentially and the other common mode.

The term "Artificial Neural Network" or "ANN" or "NN" refers to an intelligence algorithm or unit that consists of a software algorithm, implemented hardware unit or a combination hereof or the like—The ANN is used to be trained, learned, predict, recognize a pattern or the like. The term "recognize a pattern" or "pattern recognition" refers to training and/or teaching an Artificial Neural Network to be able to recognize a specific medical condition, medical circumstance, diseases, medical treatment, healthy human or sportsmen's parameters, general human behavior and/or medical parameters to optimize and achieve more accurate results, diagnosis, measurements and/or calibration or auto calibration of the Sound Sensor network.

The term "cylindrical" or "cylinder" or "tube" or "pipe" refers to any 3 dimension (3D) any oblong airflow tube/pipe such as cylinder, oblong oval, conical, square, conical and/or rectangular shaped or other 3D oblong formed respiratory pipe. FIG. 2 and FIG. 14 illustrates three different examples.

The device consists of one mother device (1) or main device, acting as a stand-alone device or base station for one or two small ear devices (210 and 211), which should be placed in auditory meatus/auditory canal. All three devices communicate bidirectionally and interchangeably (as showed in FIG. 1A (555)).

The sound sensor network device, shown in FIG. 2, may have a cylindrical body as shown in FIG. 14A, (1401) or a conical body as shown in FIG. 14B (1402) and can be made with/without a layer of sound isolation material (12) as in FIG. 2. The device has a respiratory port (2) in the front and a ventilation port (11) at the end.

The device has a modular design, which means that it is possible to couple and decouple additional Sound Sensor modules (e.g. changeable medico technique module 10) onto the body of the tube, thereby improving and expanding the collection of physiological information.

Figure 1B:
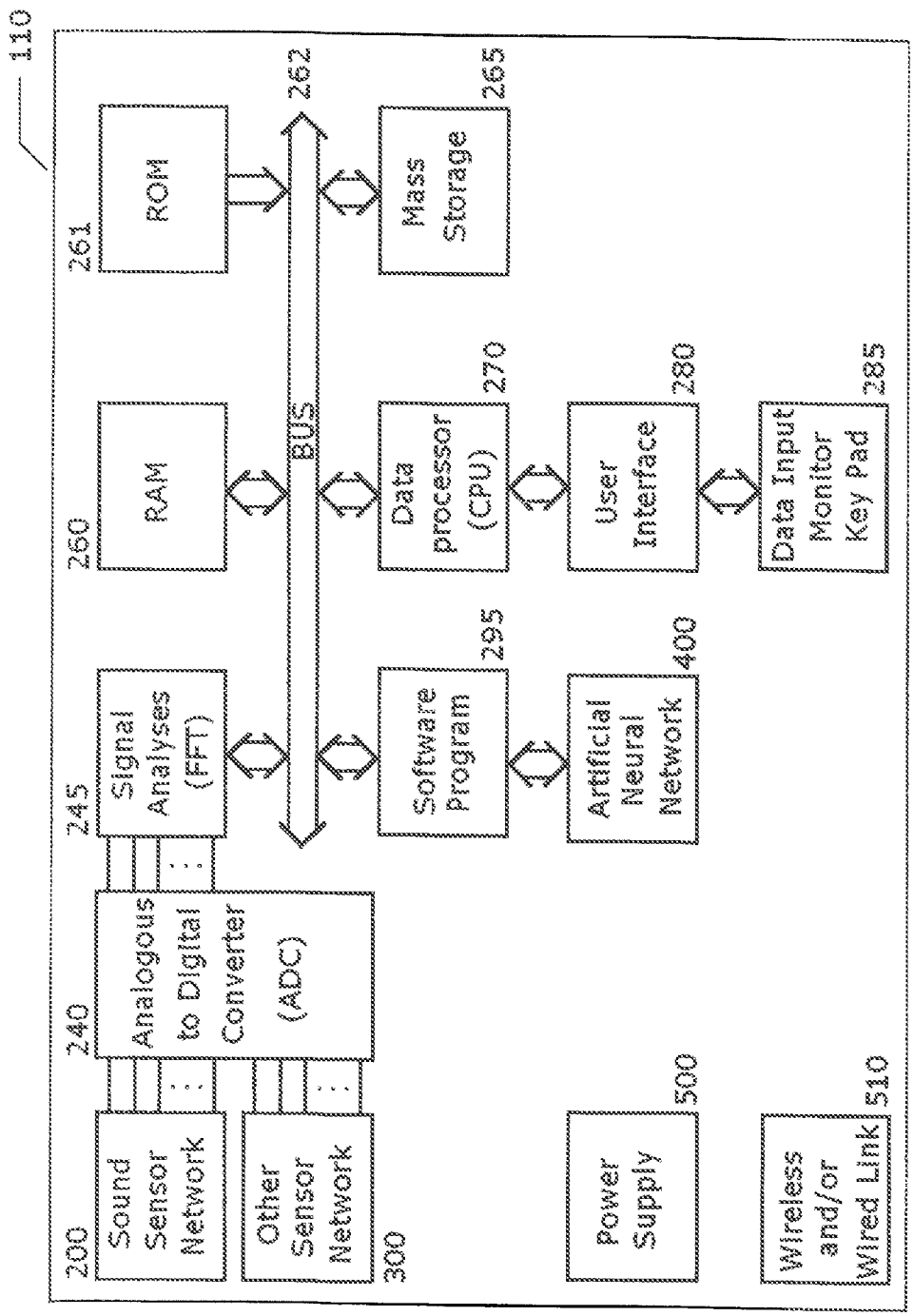
FIG. 1B illustrates the main devices internal block diagram.

All Sound Sensors will be in constant communication with the whole Sound Sensor housing through an information data bus, FIG. 1B-262, and additional Sound Sensor information can simply be obtained by clicking more sensors to the basic housing through the embedded interface plug.

As an example the respiratory sound information can be integrated with non-respiratory information collected by other type of sensors connected to the Sound Sensor network device through the sensor network data bus structure in the device, for example Bidirectional Air Flow Detector (BAFD), Flow Meter (FM), Biogas Sensors (BS), Temperature Sensors (TS), etc.

In the interior of the cylindrical, conical, square shaped or other 3D oblong formed blow pipe according to FIG. 2 and FIG. 14, the sound sensor device is built around a Sound Sensor Network (SSN) and is composed of a system, method and a neural network building upon the human or living organism's behavior.

The SSN in FIG. 1B (200) and the ear devices in FIG. 1A (210) and (211) are built around a system, consisting of one main device (1) and two ear devices (210 and 211) FIG. 5. The main device (1) acts as base station. The main device in FIG. 1A and FIG. 1B can be connected through a wired or wireless (555) connection to the ear devices. All three devices communicate bidirectionally and interchangeably through for example an electromagnetic wave (555) or a wired link, for example a cable (not shown).

Figure 1C:
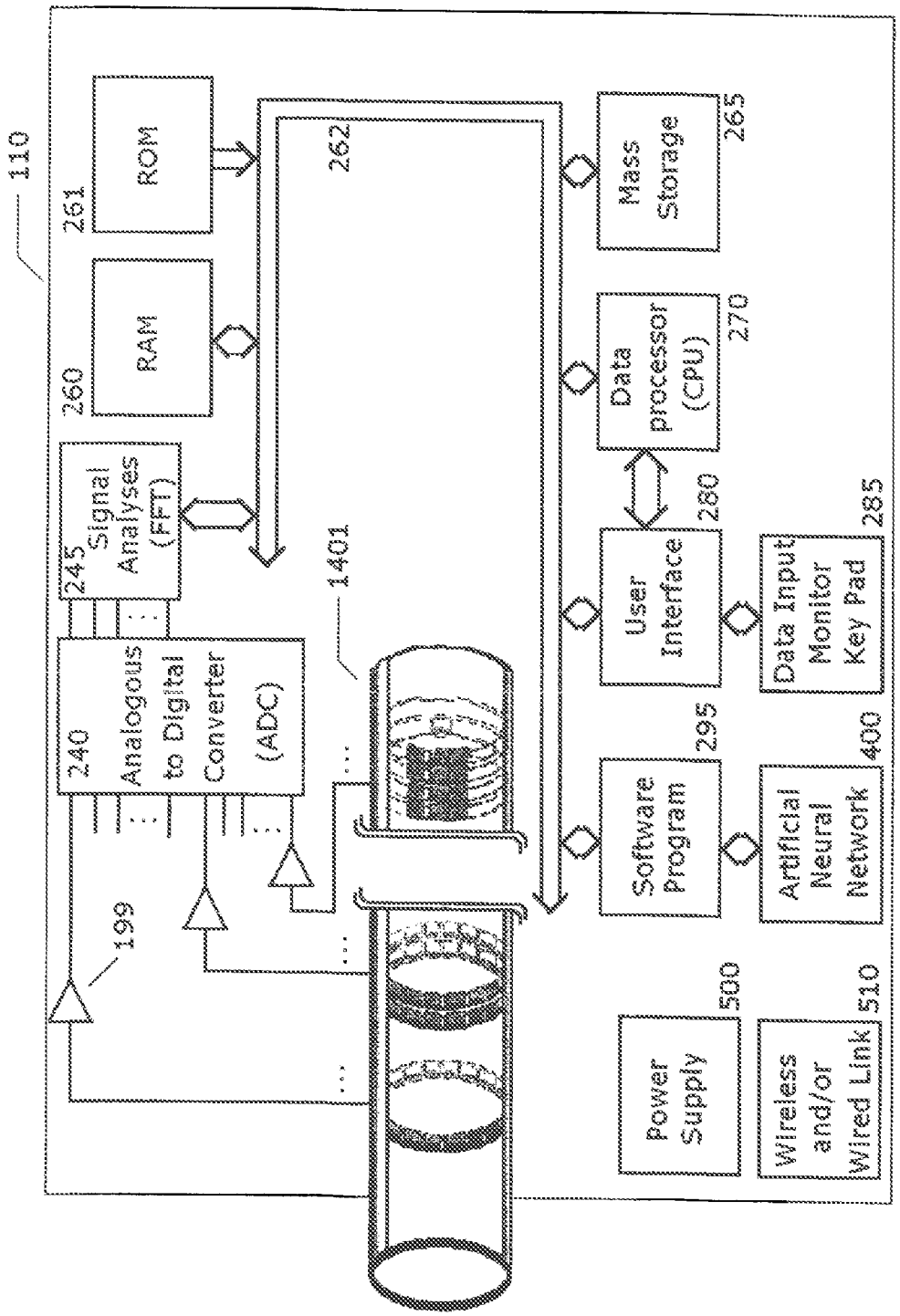
FIG. 1C is an embodiment of the device in FIG. 1A (1), containing the blocks of FIG. 1B and a tube with a sensor network as the ones displayed in FIG. 2 and FIG. 14, with a mouthpiece and filter.
Figure 1D:
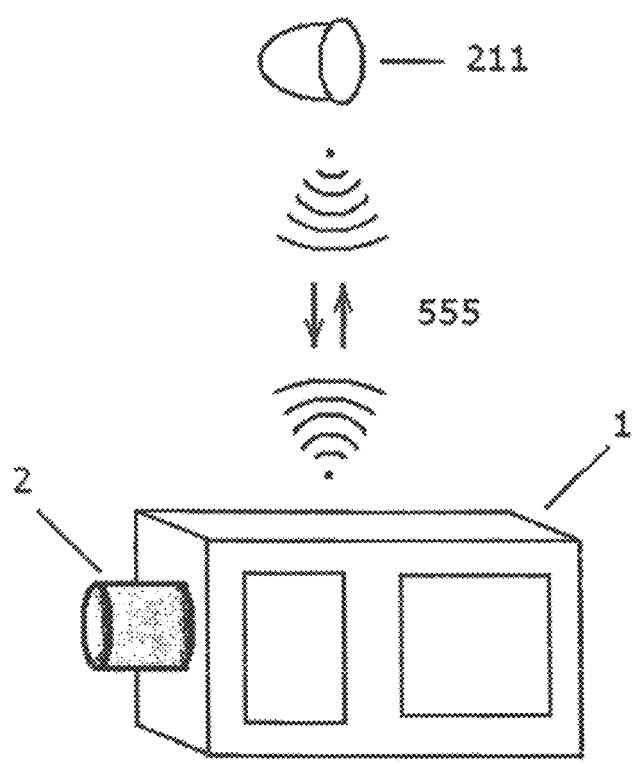
FIG. 1D shows an embodiment of the main device with a one-ear device option (left or right).

FIG. 1C shows the coupling between the sensor network, "the cylinder" and data processor unit and its peripheral units. Block (199) in FIG. 1C illustrate an amplifier, which is matched to a sensor. These amplifiers are not shown in FIG. 1B and ear devices FIGS. 5A and 5B.

The main device in FIG. 1A (1) may be connected to ear devices (210) and/or (211) or disconnected from both of them. In this sense the main device may act as stand-alone device. There are five different connection modes for connecting the mother device and the ear devices. The mother device in FIG. 1A (1) may act as stand-alone device, the mother device may be connected to both ear devices (210) and (211), the mother device may be connected to the right ear devices (210) or the left ear device (211). In the last mode i the connection between main device and ear device (210) and/or (211) is regardless of the position of the ear device(s), i.e. no registration of light and/or left position, regardless of there is single ear device or both of them.

The main device can determine if it has been mapped to the right device (210) or the left device (211) and the positioning of the ear devices should be provided by the user. Alternatively the ear devices may be found automatically by t h e main device. This is why two different setup modes can be installed by a user or a doctor to the main device for this purpose.

Figure 5A:
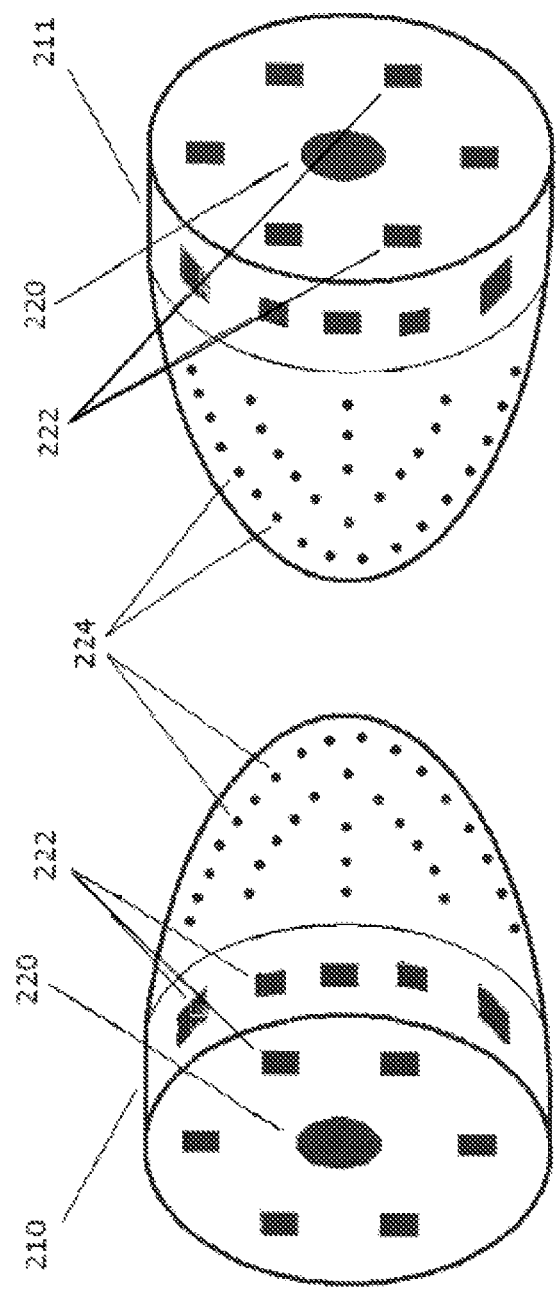
FIG. 5A The ear devices, the right ear device 210 and the left ear device 211.
Figures 5B, 6:
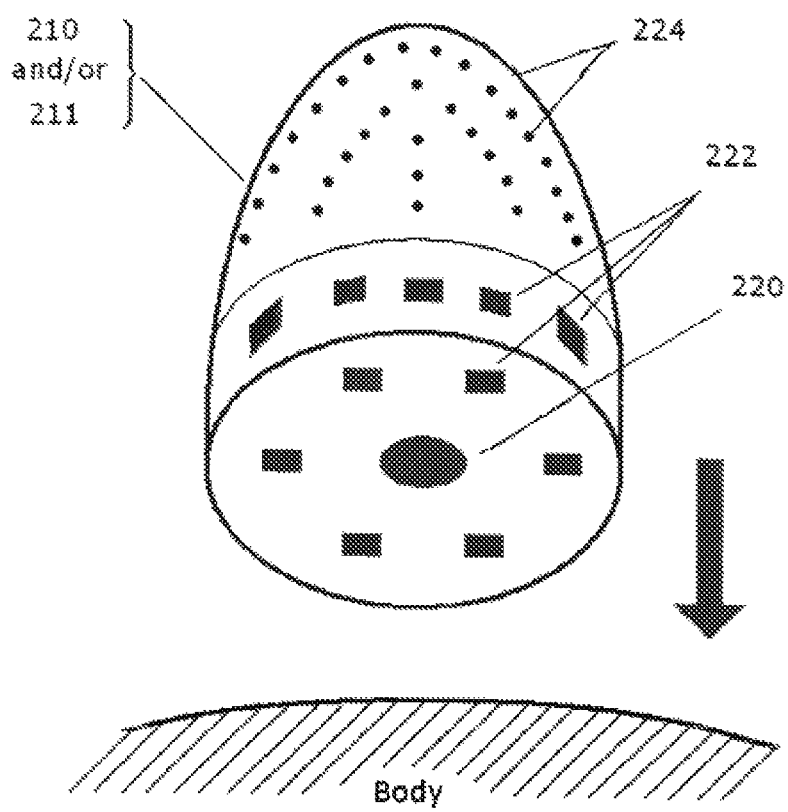

By ear device (as shown in FIG. 5A and FIG. 5B) is meant a device, consisting of Sound Sensor Network and other sensor network, such as Temperature Sensors and/or Pressure sensors and/or Moisture Sensor (any of these sensors represented by 224 in FIGS. 5A and 5B) and/or Sound Reproducer (not shown) for example a speaker, which should be placed in auditory meatus/auditory canal or earpiece. After collecting, mapping or handshaking between the devices, the information from the ear device will be amplified, digitalized and sent to the mother device through a wired or a wireless connection as shown in FIG. 1A. The ear device collects lung sounds and these respiratory sounds are used for compensation environmental or improve the Signal to Noise Ratio for a given measurement/signal in noisy conditions or for achieving more precise measurements for example in case of clinical use with higher requirements on accuracy.

The ear devices 210 and 211 are identical except their positions and algorithm to map them to the main device, which enables the possibility to identify them as right and left device.

The Sound reproducer can for example signal an error to a user during the measurement procedure, for example by displaying an error message through a miniature microphone or the like. The user has an option setup to communicate/signal to the device by speech or by pressing/changing a pressure through the Eustachian tube, which will act or confirm. The speaking can be understood by ear device(s) without any need of taking the ear device out of the ear.

The mother device can also ask, through a sound reproducer or digital display or the like, the user to place and keep one or both ear device(s) to a specific area of the body. These body areas can be pointed out by a doctor or a user manual of the device. These body areas can for instance be around heart, wrist, lungs stomach, neck, throat or the like.

The ear device, connected to the mother device, can optionally serve as a radio receiver, transmitter and/or transceiver and the like and/or music player, for instance an MP3 player or the like.

The information to the sensor network may be collected from a user through a mouthpiece device FIG. 1A (2) and further through a pipe (shown in FIG. 2).

The sensor network FIGS. 2, 3, 4, 5 and 8 show embodiments of sound sensor network 5, 6, 7 or the like. Additional Sensor networks are also possible (see e.g. FIG. 8, (801, 802, 140 and 143)) and these can be flat or have any 3D form and may also be Mounted Surface Micro- or nanotechnology sensors. FIG. 8 shows an elongated/oblong plus (+) shaped (cross-section) sensor network that could also have any flat (−) or 3D shape, for example an elongated/oblong plus shaped (cross-section), bent as a spiral or a similar shape.

Figure 9A:
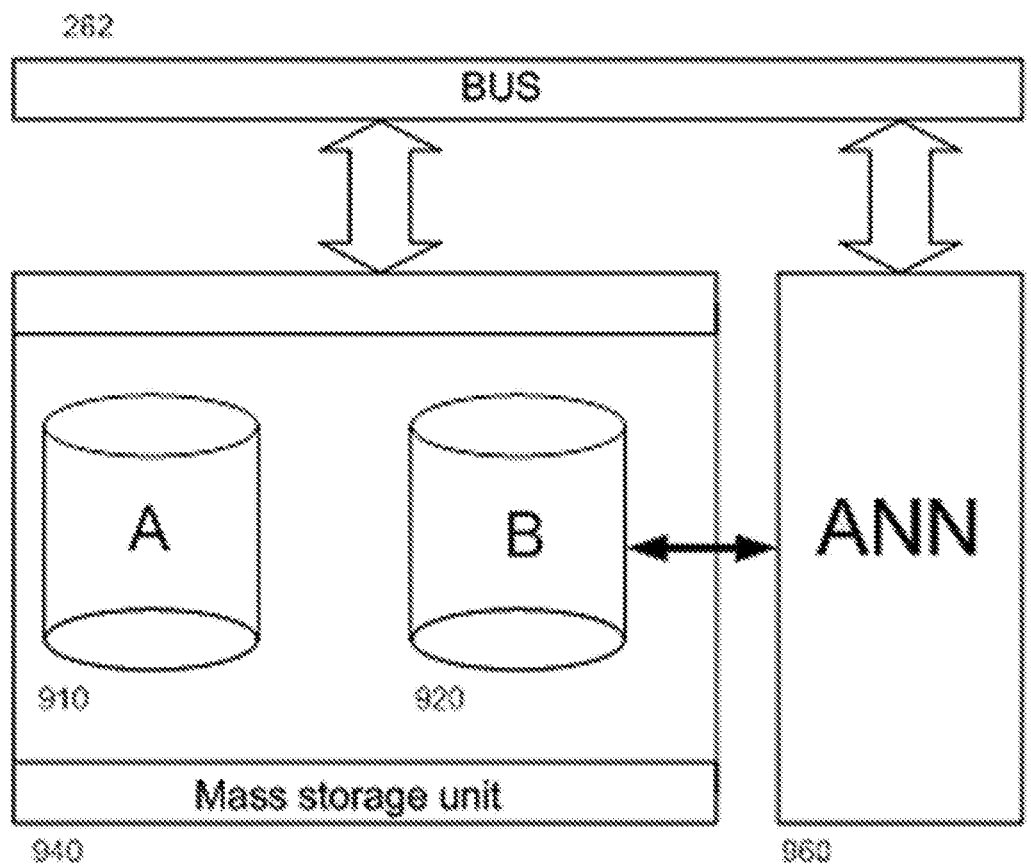
FIG. 9A shows a Mass Storage Unit, where data is stored, a data bus and an ANN unit.
Figure 9B:
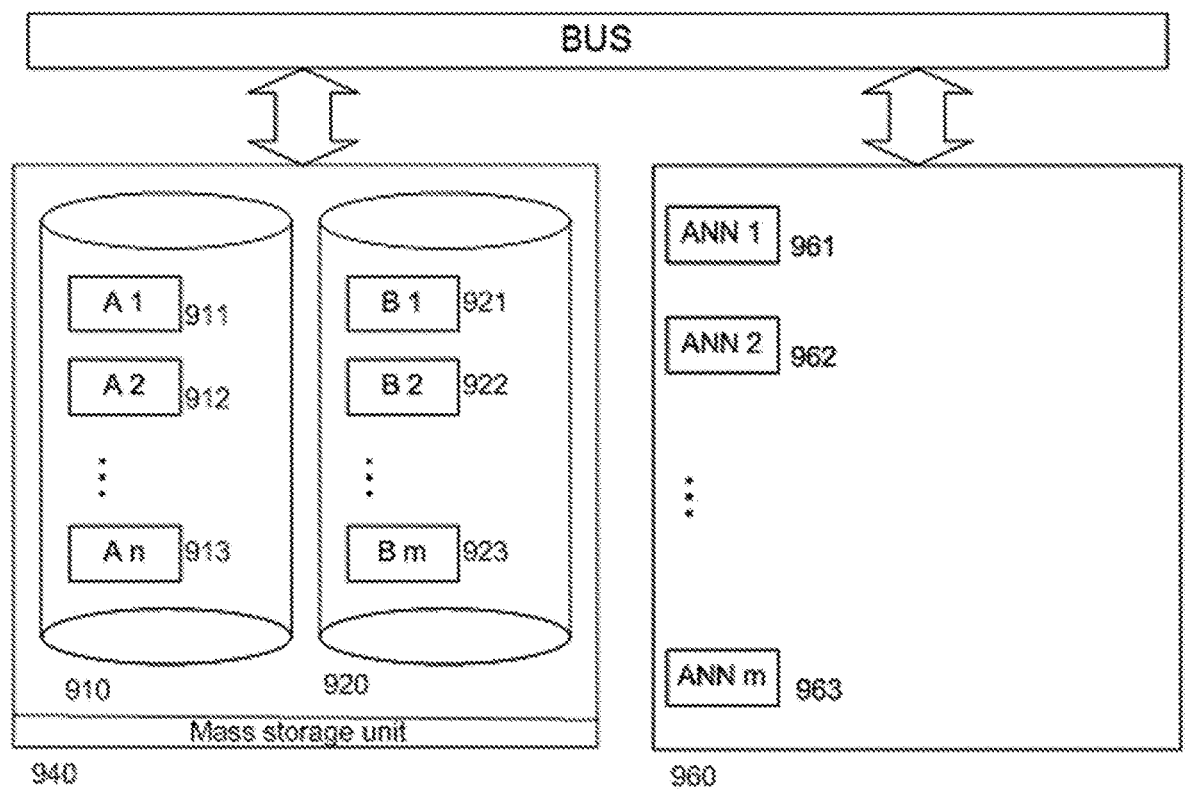
FIG. 9B shows a Mass Storage Unit, where data is stored, a data bus and an ANN unit.

The data is stored to the Mass Storage Unit 940, FIGS. 9A and 9B, through data bus 262. Mass Storage Unit A, shown as block 910 is a read only memory and includes all input data with date and time stamps.

Mass Storage Unit B, shown as block 920, is used to store the gained information. The stored information is processed in ANN block 960. Blocks 911-913, 921-923, 961-963 show every single unit of 910, 920 and 960. The number of units may vary. FIG. 9A as well as FIG. 9B have only illustrative purpose.

The device is able to establish communication to an external data processor through a wireless connection (510) or a wired (not shown) link such as USB, Bluetooth, Infrared etc., similarly transmit and receive data to and from the data processor and the result may be stored into a memory or database via a software or hardware interface and/or both, locally or on an internet server.

The collected information can be shown as real time curves on a display, monitor, or any other type of display or external device, for example PC, laptop, PDA or the like, or by printing a curve through a wireless or wired link as shown in FIG. 1 (510).

The system and methods are flexible in their design and independent upon the type of disease. This means that the system can be adapted for several types of measurements, just by changing the loaded software with respect to which (the changeable) sensor network module (5, 6, 7 and 810) are used.

The apparatus is capable of allowing a given user access to an automated process for managing a specified health problem, disease, improved life condition and earlier prevention of disease. These benefits are obtained primary by storing and analyzing respiratory sound information through the Sound Sensor Network and the Artificial Intelligence data processing.

The analysis of the sound is based on the idea that the respiratory sounds are unique and could be used for asthmatic and allergic sicknesses diagnosing. That makes the usage of sound analysis reasonable for the purpose of personalization of the device. The respiratory sounds, produced by a user, should be registered in both time and frequency domain and stored to be used for sickness diagnosing, for creating the users condition history, which could be accessed in form of data tables and curves, and later for the prediction of the users condition.

Furthermore, the system and method relates to automated self-measurement and analysis of respiratory sound information from living organisms.

Another aspect is directed to allowing a user access to an automated process for managing a specified health problem called a disease.

The related system and the method for its use are used for imaging and/or guidance and/or diagnosing and/or controlling purposes and are capable of communicating with external data processors, for example PCs, Laptops, PDAs, Mobile Phones, etc. through a wired link or wireless connection.

More specifically the combined sensor modules, system and their methods of use relate to a personal handheld home monitoring device, acting as an intelligent portable system and employing methods related to specific health issues.

Furthermore, the device is generally capable of being used as a medical journal, data acquisition, storage of measurements, medicine optimizer, monitoring, night monitoring, night surveillance, storage of provided and/or calibrated personal input data and user health behaviors, as well as short time or long term data acquisition, storage and analysis.

The functionality of the apparatus could be described as follows: When the device is turned on for the first time or the device's master reset is activated, the device will run the initial routine, part of this routine shown as an example in FIG. 7A. During this process a user will be guided through the instruction to answer a number of questions, which will be displayed on the display, played by a media from the device or from a display and/or media that is coupled to the device for this purpose.

After calibration of the sensors and the network constellation and start-up mode 793, personal data 795, relevant health information 797 and information about medicine 799 should be entered, displayed sequentially in 890, 803 and 805, corrected/confirmed by running the correction algorithm if necessary in 807, 809 and 811 and saved and stored in 813, 815 and 817. The subroutine ends in 819. Personal data and health/medicine information could contain ID (name and number), sex, age, height, weight, smoking habits, illness, usage/dosage of different medicine, additional keyed/uploaded data and optional data, information from the doctor or hospital, allergy and pal, etc.

All these input information/data will be stored in the device. The device will use this information to calculate the user's medical, physiological status and other parameters, e.g. standard values or reference values such as Body-Mass Index (BMI), PEF, FEV1, FEVa, FVC, VC, etc. A few examples of reference/standard values are mentioned below ((Berglund E, Birath G, Bjure J, Grimby G, Kjellman I, Sandquist I Soderholm B. Spirometric studies in normal subjects. I. Forced expiroprograms in subjects between 7-70 years of age. Acta Med Scand 1963; 173: 185-192; A J Nunn, I Gregg, "New regression equations for predicting peak expiratory flow in adults"—concerning this article more than 20 references at all could be named and incl.).

For Girls:

$$\log_e \text{FEV1} = -1.5974 + (1.5016 + 0.0119 * \text{age}) * \text{height},$$

$$\log_e \text{FVC} = -1.4057 + (1.4800 + 0.0127 * \text{age}) * \text{height},$$

$$\text{FEV}_1 \% \text{FVC} = 88,88$$

For Boys:

$$\log_e \text{FEV1} = -1.2933 + (1.2669 + 0.0174 \cdot \text{age}) * \text{height},$$

$$\log_e \text{FVC} = -1.2782 + (1.3731 + 0.0164 \cdot \text{age}) * \text{height}$$

$$\text{FEV}_1 \% \text{FVC} = 86,21$$

For Females:

$$\text{FEV1} = 1.08 * (3.95 * \text{height} - 0.025 * \text{age} - 2.60)$$

$$\text{FVC} = 1.15 * (4.43 * \text{height} - 0.026 * \text{age} - 2.89)$$

$$\text{FEV}_1 \% \text{FVC} = 89.1 - 0.19 * \text{age}$$

$$\log_e \text{PEF} = 0.376 * \log(\text{age}) - 0.0120 * \text{age} - (58.8/\text{height}) + 5.63$$

For Males:

$$\text{FEV1} = 1.08 * (4.30 \cdot \text{height} - 0.029 * \text{age} - 2.49)$$

$$\text{FVC} = 1.10 * (5.76 \cdot \text{height} - 0.026 * \text{age} - 4.34)$$

$$\text{FEV}_1 \% \text{FVC} = 87.2 - 0.18 * \text{age}$$

$$\log_e \text{PEF} = 0.544 \cdot \log_e(\text{age}) - 0.0151 \cdot \text{age} - (74.7/\text{height}) + 5.48$$

This information will be stored and compared to the measured data later and stored again. All data entries are given a date and time stamp in the store unit.

During use the device may gain more information about the specific user through measurements and through communication between the user and the device. It will result in that the device will achieve more accurate information about the user, therefore the reference or standard values will be not used anymore, nevertheless maintained on the device storage unit. The user has always access to all this information, but the user is not allowed to change, delete or overwrite the data once they are stored, thus the information is part of the Artificial Neural Network (ANN) resources. Although ANN has an adaptive character, the data collected will be saved in the device and could be accessed later in order to review a users condition. After a given period of time, when the device may learn more about the user by collecting, compiling and storing data from the user. All data entries get a set of date and time stamp.

When a measurement procedure is activated or if a timer is activated and set to give periodic alarm indications to remind the user to perform a given measurement, the device will run a program and algorithm internally and afterwards the user will be guided throughout the process to take one or several measurement(s). The alarm will indicate the measurement event by text on display, sound or voice from the speaker, light an LED, shake alarm (vibrator) and the like.

Measurements are then started and the program will run. An example of a routine is illustrated by FIG. 7B (main routine) blocks 701 to 735 and FIG. 7C (subroutine), blocks 737 to 753. In this particular example in FIG. 7B, the system starts with block 701 and request for the deep breathing program. The device goes into measurement mode 703, where subroutine 737 (FIG. 7C) is called. The type of the measurement mode is classified in 739, and the test begins with internally defined Flow Meter (FM) mode, where all measurements are taken in the process of not forced inhalation and exhalation. Then the temperature ° C., FMin (inhalation parameter) air flow, FMout (exhalation parameter) air flow, lung sounds (wheezing, crackles, snores, etc.) are registered and $\text{FEV}_1$, $\text{FEV}_6$ and FVC calculated in the block 745. In the mode of forced inhalation and exhalation PEF, FEV1, FEVs and FVC are registered. If the measurement is a PEF type, the user is asked to perform a maximal expiration three times, each expiration followed by a rest period (usually 1 minute).

The PEF value is calculated in 745 for the three tests and the values are checked for some reliability criterias in 749. If the criterias are fulfilled the value(s) are stored in the memory 753, but if they fail the user is asked to redo the measurement. The PEF measurements are usually done three times with 1-minute intervals between the measurements.

If the measurement is of the second type, the user is asked to perform a maximal forced expiration in 743 at least three times. The values are also checked for some reliability criterias in 751. If the criterias are passed the value(s) are stored in the memory in 753, but if they fail the user is asked to redo the measurement in 753.

All the $\text{FEV}_1$, FEV6 and FVC values are then calculated and stored in the memory.

The essential part of this procedure is that it can minimize the measurement errors caused by wrong use of the device when used for home measurements. This minimization of measurement errors is achieved by requiring the measurements with high accuracy.

The measurements flowchart are only illustrative, many different types of measurements can be performed in conjunction with this device.

Figure 7A:
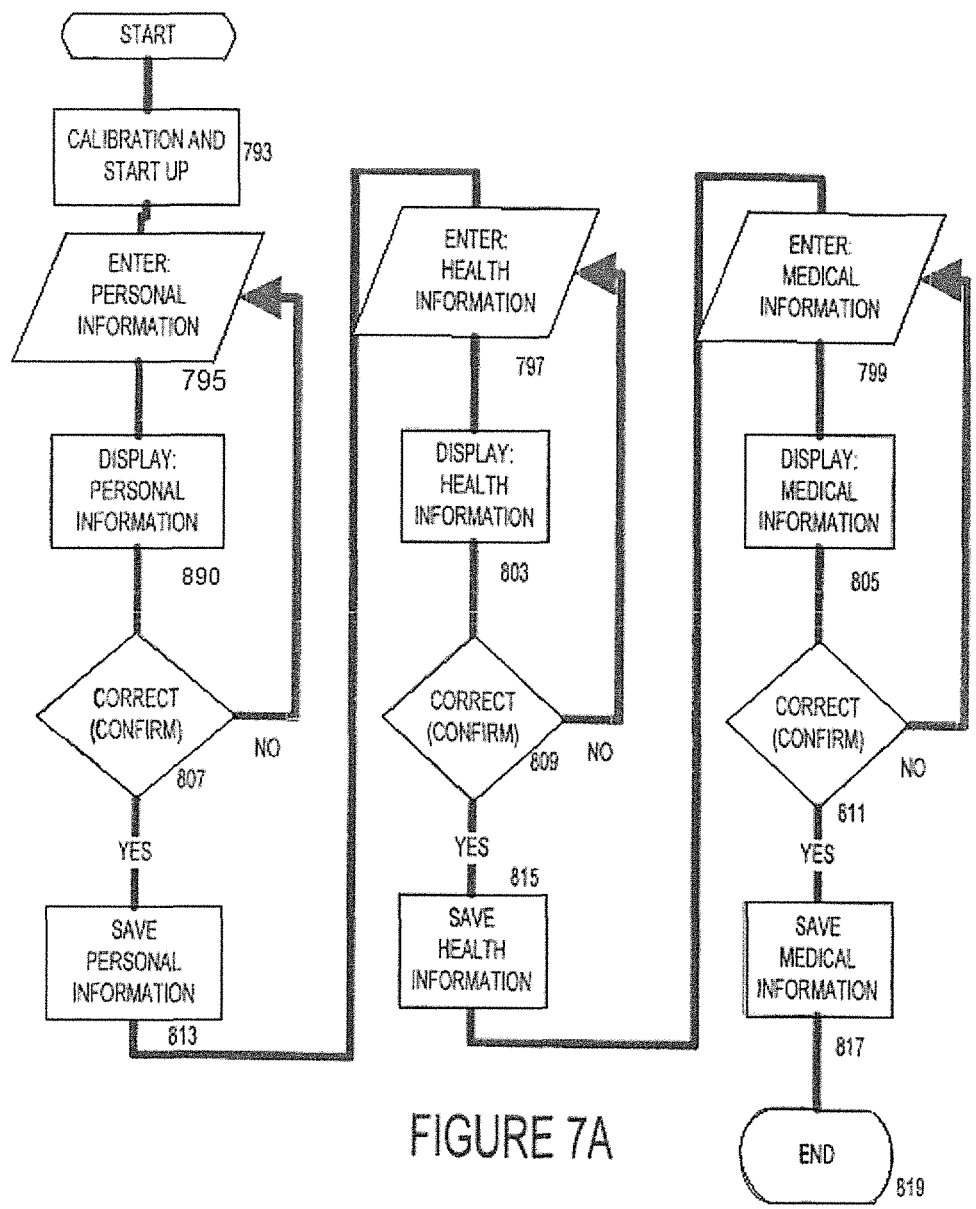
FIG. 7A Flowchart of a subroutine for initial data input.
Figure 7B:
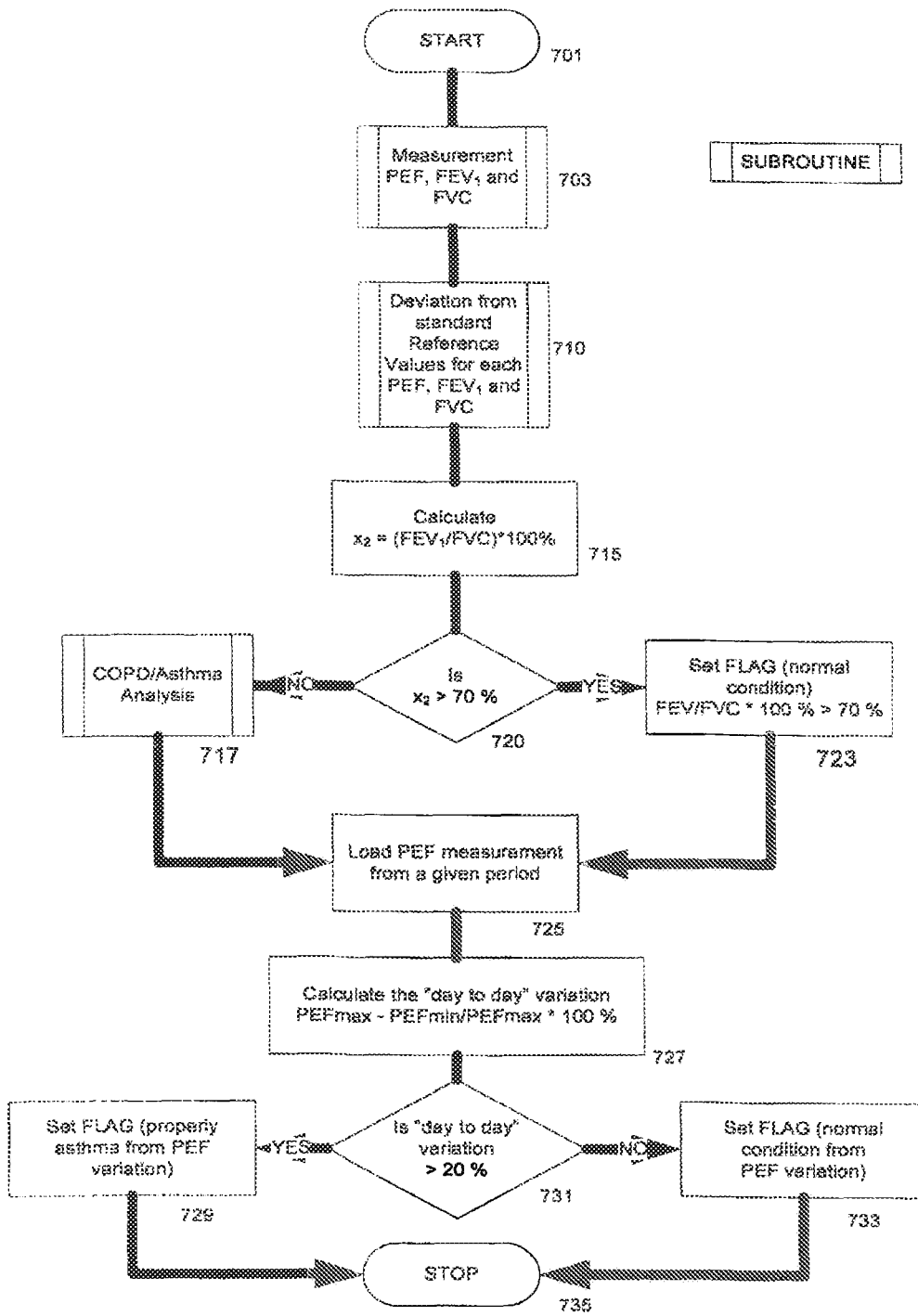
FIG. 7B Flowchart of a subroutine for COPD/asthma diagnosing.
Figure 7C:
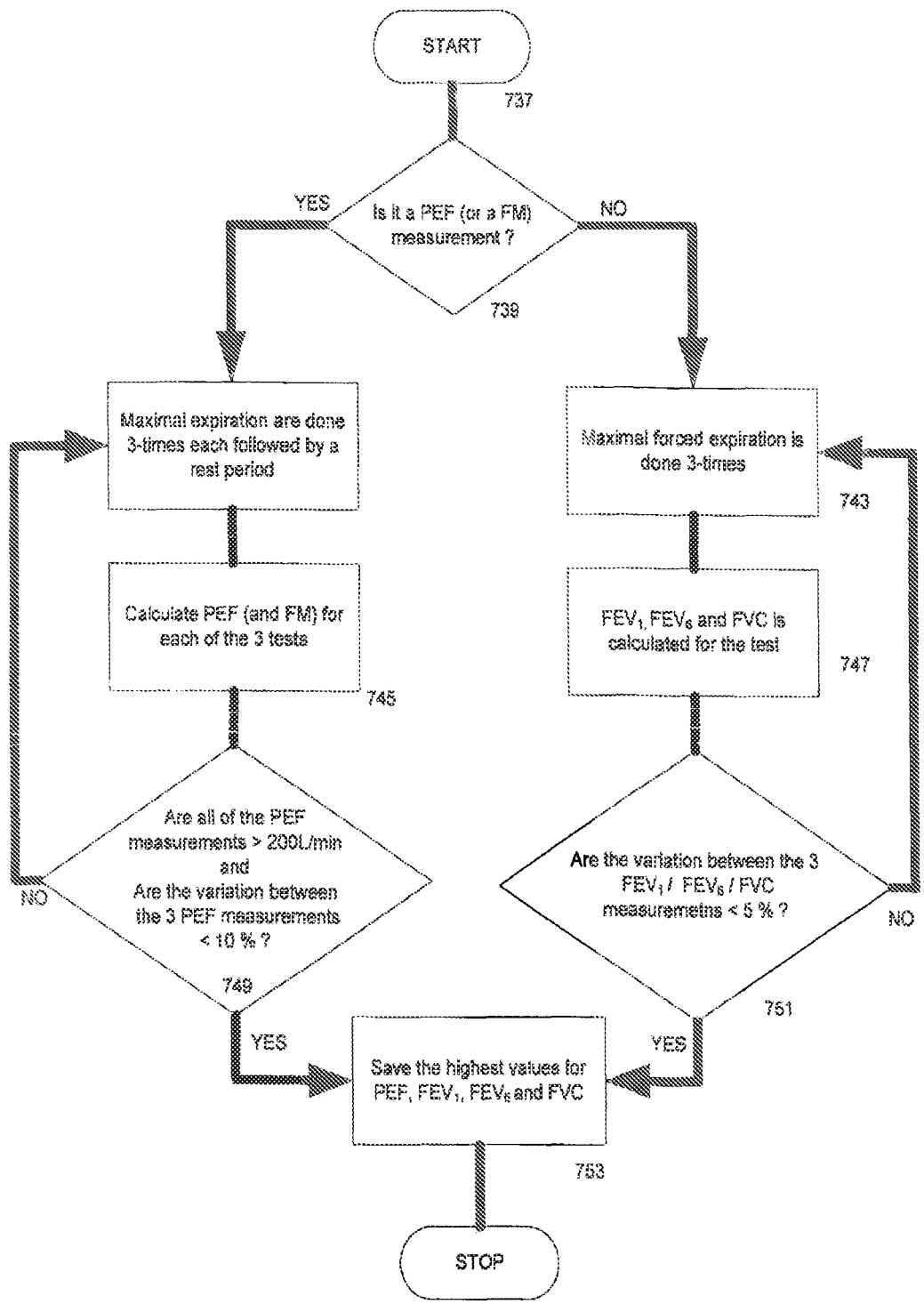
FIG. 7C Flowchart of a subroutine for measurement of PEF, FEV1. FEV6 and FVC.
Figure 7D:
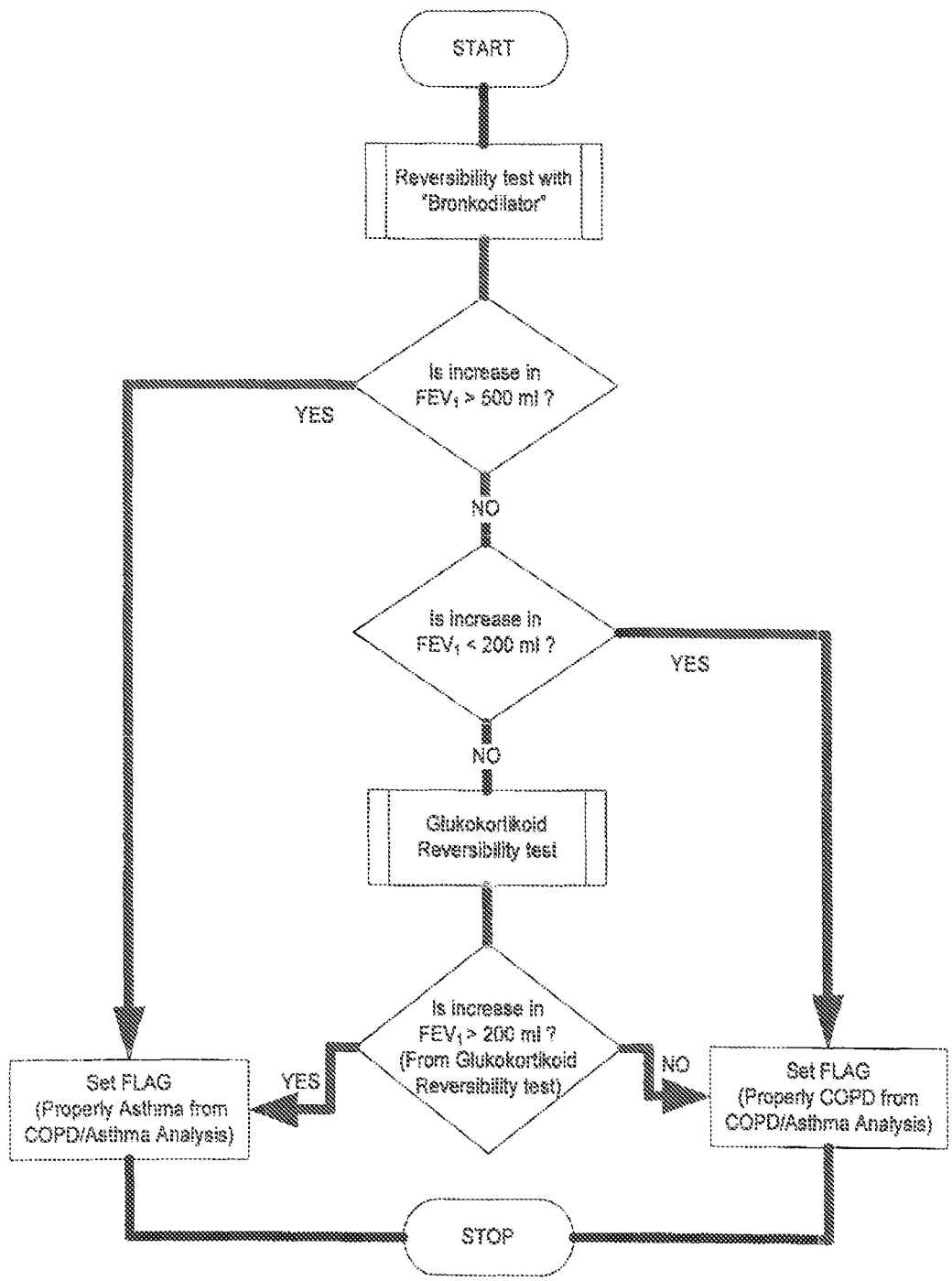
FIG. 7D Flowchart of a subroutine for Reversibility with emphasis on COPD/asthma diagnosing.
Figure 7E:
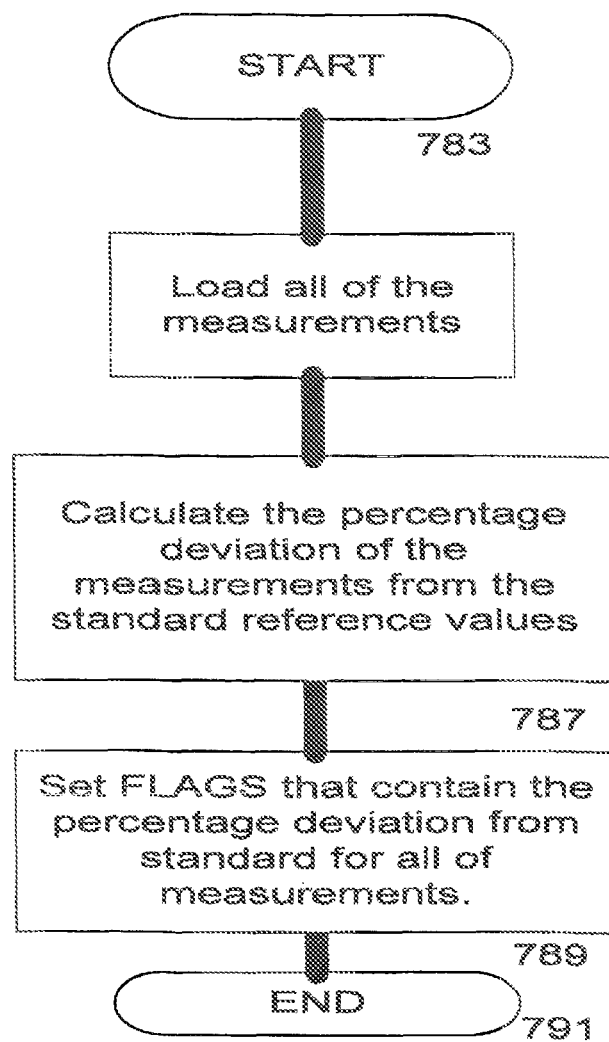
FIG. 7E Flowchart of a subroutine for user data/information managing and calculating the percentage deviation of the measurements from the standard reference values and Sound Sensor network calibration via ANN.
Figure 7F:
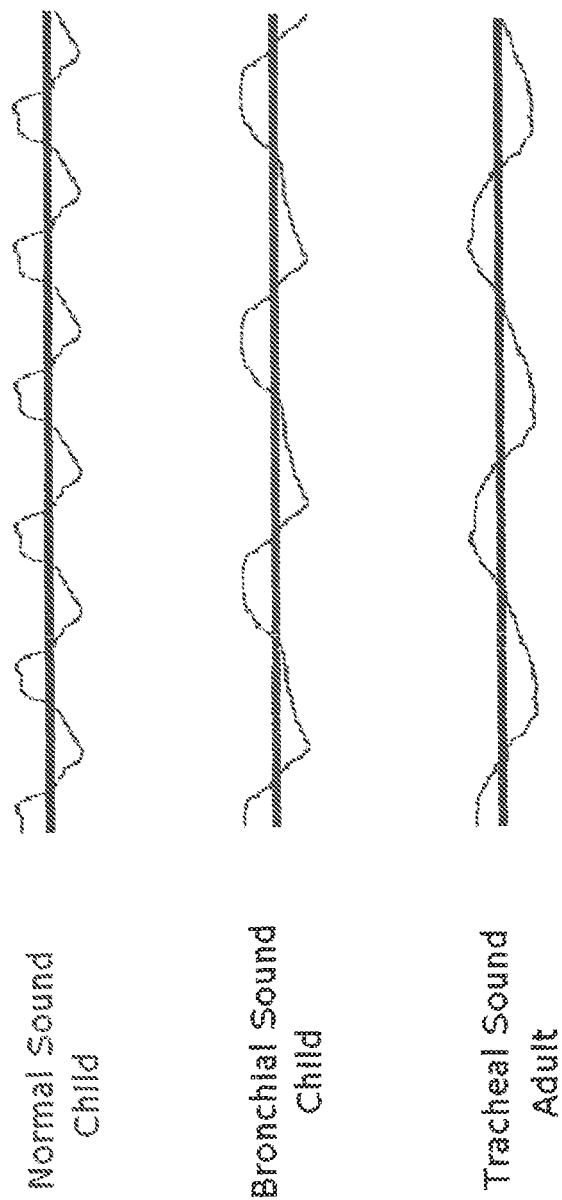
FIG. 7F Examples of lung sounds.

Comparison of the measurements with standard reference values 710 starts in 783 in FIG. 7E. After loading data in 783, calculation of the percentage deviation (787) and setting indications flags containing the percentage deviation for each of the measurements (789) are performed and end in 791.

Calculation of $\text{FEV}_1/\text{FVC}$ ratio (715) by formula ($\text{FEV}_1/\text{FVC}) \cdot 100\%$ is performed in order to set asthma/COPD diagnosis. Please notice that the apparatus does not provide the medical diagnosis. However a diagnosis by a doctor could be based on the date collected and analyzed by the apparatus. If there are any signs of illness found in process 720 (more than 70% for a healthy human), indications flags 723 and 717 are set. These flags can then be used by the physician in his overall diagnose of the user of the device. After loading PEF measurements in 725, day per day variation 727 is calculated by formula $\text{PEF}_{max} - \text{PEF}_{min}/\text{PEF}_{max} \times 100\%$. The percentage deviation 731 defines indications flags 729 and 733. The procedure ends in 735.

A simple realization of a display can be a digital display, an LCD on the device itself or a display that is connected to the device for this purpose, such as mobile phone, PDA, Palm, Laptop, PC or the like through a wired or wireless connection. A simple realization of voice based media can be a simple speaker that is mounted on the device itself or a voice based media that is connected to the device for this purpose, such as mobile phone, headset, hearing aid, PDA, Palm, Laptop, PC or the like through a wired or wireless connection. It is possible to encrypt this information to protect the users personal data and information. This facility is not shown.

The intelligent part of the device is based on Artificial Neural Network (ANN). ANN takes as input the data measured and is trained to recognize the specific user behavior, a given pattern as mentioned below, which makes the device highly personalized. It also includes sound analysis.

Lung sounds produced by a user are unique and can be used for COPD/asthma behavior prediction. When the user has difficulties to breathe because of asthma, the problem is in the airways of the user lungs. The airways become narrow because the muscles around them tighten, their inner linings swell, and extra mucus clogs smaller airways. Breathing gets harder as user try to force air through the narrower airways. The air the user breathes may make a wheezing or whistling sound.

After the end of a learning period the device should be able to know more about the specific users behavior pattern, i.e. possess more accurate data etc. Thus the device should be capable to estimate, calculate, recognize, calibrate and correlate exactly the value of different measurable parameter for a users condition and should be able to correlate for the measurements values by analysis of lung sound and few other parameters and calculation and estimate other washable measurement values.

The Use of Artificial Neural Network (ANN) in Software Development and its Goal Setting:

When the Device according to FIGS. 1A, 1B and 1C, is turned on, the device automatically goes into self-test mode as shown in FIG. 7A. Hereafter an initiation process is performed, which is followed by test & calibration of the sensor network and checking the data. Then the device goes automatically into Flow Meter Mode (FMM), and asks the user to breath normally through the mouthpiece until device indicate for second phase of measurement. Afterwards the device indicates that a second measurement should be performed, and the user is asked to breathe deeply through the device, similar to when a doctor listens to a patient's lung with a stethoscope. During these measurements the user should be sitting, standing or lying relaxed and breathe normally, i.e without forcing.

The device will measure a users bidirectional inhalations and exhalations and subsequently measure, calculate and store different important parameters such as lung sounds (both in time domain and frequency domain), vital capacity (VC), temperature of lungs (see below), etc. These parameters will be measured, registered, checked and saved. The same should be done when the device goes into measurement mode (FVC, FEV, etc.), performed on the condition of forced breathing.

The users unique and personal parameters will be learned and stored by a learning progress, through the device's Artificial Neural Network module. The algorithm should remember given patterns to determine the users condition when he is relatively healthy ("normal" condition) and relatively sick ("abnormal" condition). For every FM mode the device, with help of the ANN, should guess the user's condition and after completing measurement mode the device should compare the guessed data with the measured data. The idea is that when this comparison indicates an error percentage less than 2%, the device will be able to predict the users condition, e.g. COPD/asthma behavior, every time it goes into FM mode. This will help a user to prepare himself for sicknesses "peaks" and "quiet" periods as well as to administrate own medication. Another purpose is to remember the users data patterns in order to precise the measurements. Existing apparatuses are usually 90% precise, whereas the device with help of ANN should be closer to about 98%. This will help to diagnose a user more precisely as well as administrate medicine doses with higher precision.

Figure 13:
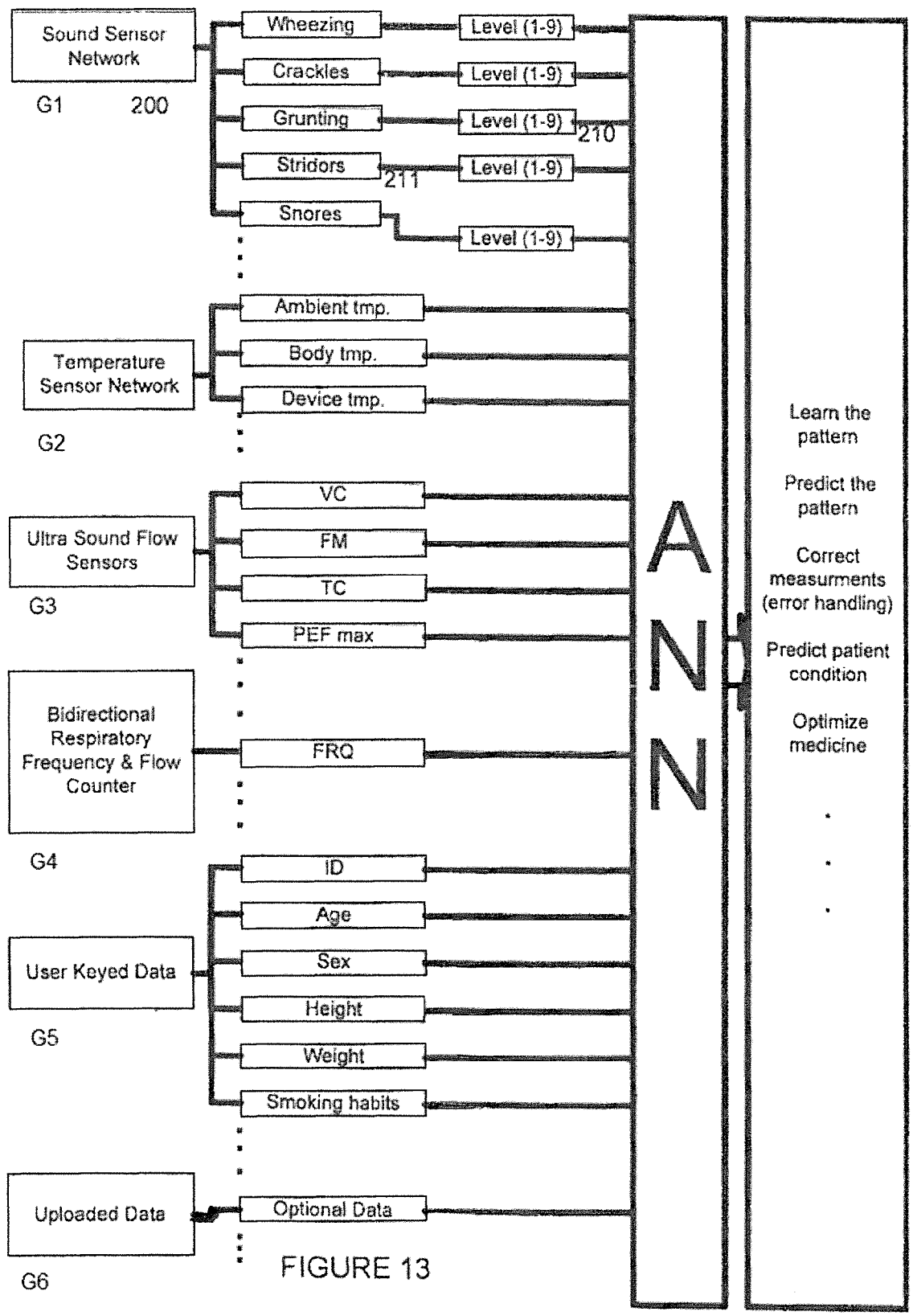
Figure 15:
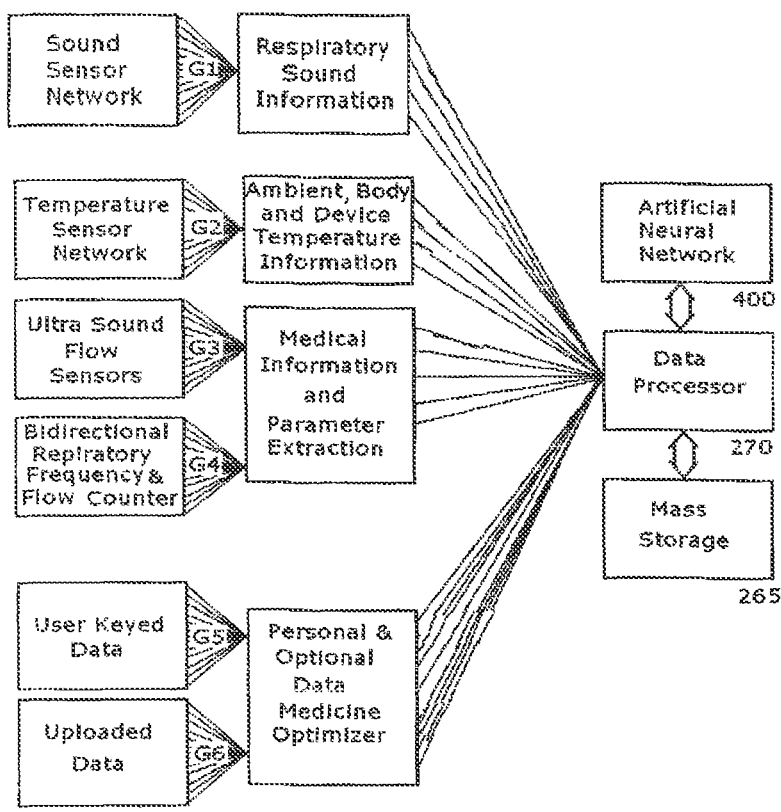
FIG. 15 ANN and the Sound Sensor network groups G1 to G6 and a data processor.
Figure 16:
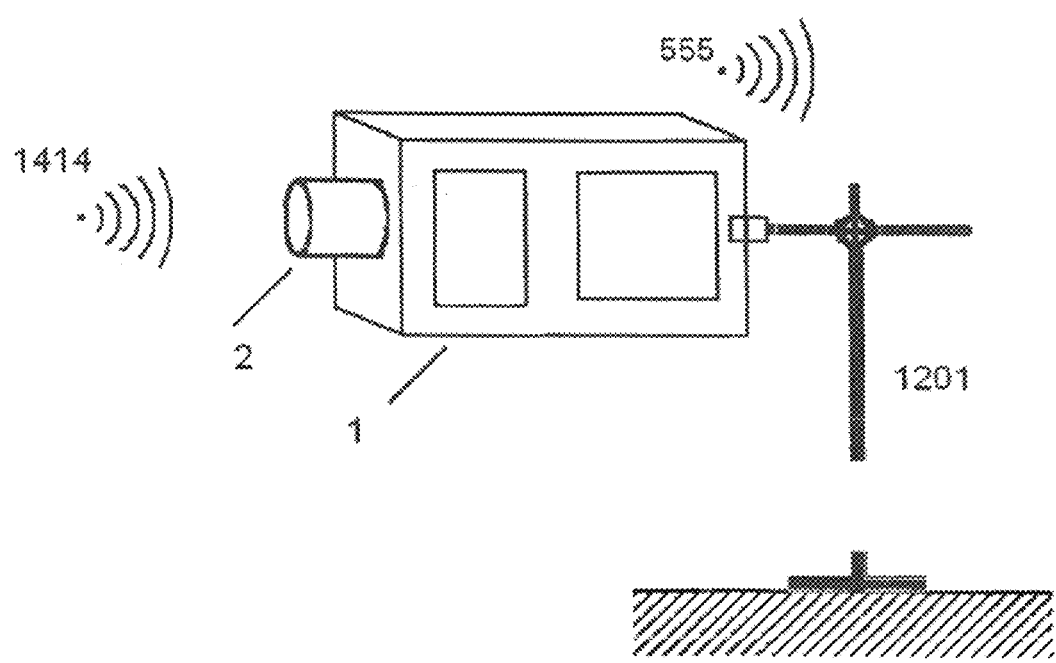
FIG. 16 shows a setup of the mother device (as well as the ear device). Block 1490 shows a sound signal. The apparatus is able to analyze an incoming signal and transmit a result. Block 1201 shows a stand for holding the device.

There are 6 groups of inputs, G1-G6 in FIG. 13, to create data patterns for ANN learning/training and further pattern recognition.

Furthermore, those time series could be treated as input files for ANN, using back propagation (general solution), fuzzy logic, simple linear ANN or other types of network. The possible structure of the desirable functionality is shown in FIGS. 9, 10, 11, 12, 13 and 15. Some of the input parameters are shown in FIG. 13 and should not be taken in a limiting sense as they are only illustrative—many other parameters could be deployed in the later versions.

The displayed or oral instructions may be answered by for example the user, doctor, or hospital staff by means of keypad, dictated command or other form for indication. This information, the answers and the input data etc. can also be uploaded to the device by the user himself or by a doctor etc. via a wired or wireless connection 510.

The classification of information is achieved through the commutation between the user and device, comprising classifications such as the user's physical condition, psychological condition, allergy specification and the degree, headache and its interaction, pulmonary condition, respiratory condition, mood, "low spirits", happiness or other related pattern that is important for user. Other parameters are users' own behavior or users' reaction on an external parameter such as weather, a given condition, house-dust mite, different smoke or gas, food or drink/liquid and the like and their interaction.

The optional part of the device lets the user set the device up to learn, recognize and optimize a given condition, parameter or behavior. Also a medical condition, a parameter related to medicine, pollen or other parameters which the user wishes to learn more about or administrate may be setup by the user.

After setup of the device for first time or after master reset activation and a new setup setting, there is possible for a doctor/specialist to choose a specific input data/parameter not to be taken in account for optimization in the ANN training progress and classification. The reason for this option is if a certain parameter is not allowed to by ANN optimized in a specific country. Similarly it is possible for a physician/a doctor or specialist to choose a specific parameter to be taken into account for optimization in the ANN training progress, but for a given specific period, for example 14 days, a month or the like, for example for achieving more accuracy or better calibration of the device. After the expiration of this period the device will not be able to optimize the specific parameter.

The term "User" shall refer to a patient, person, adult, child, sports person and/or living organism as well as healthy and ailing person.

The lung(s) sound can be generated during sleep, under narcosis, coma or during unconsciousness. The term "sound" here and in the following is used to denote wheezing, crackles, snores, grunting, striders or the like and shall also refer to other sensor networks not related to sound.

The expression "biogas" shall refer to all exhaled gases, atmospheric gases, and other gases or vapors relevant to asthma patients, such as NO, $H_2O_2$, $O_2$, $CO_2$, CO etc.

The expression "humidity" shall refer to humidity in general terms, the humidity or vapor in the atmosphere, and exhaled gases exiting the user's body e.g. from the mouth, the nose and the ears. These gases comprise liquid particles e.g. $H_2O$ and $H_2O_2$ particles and the like.

Whether mother device is paired to the right ear device (110) or the left ear device (111) and the positioning of the ear devices can be provided by the user or detected automatically by the main device. For this purpose there are two different setup modes that can be installed by a user or a doctor on the main device. Ear device (FIG. 1 blocks 110 and 111) shall refer to a device, consisting of a Sound Sensor Network (SSN) and other sensor networks. These sensor networks can be a combination of any of the following according to the requirements of the observation:

1. Temperature sensors
2. Pressure and flow sensors
3. Moisture sensors
4. Sound and vibration sensors
5. Biogas, biomedical and/or electrochemical
6. Optional detectors In addition hereto, a sound reproduction device, e.g. a speaker, is placed in the auditory canal (meahus) or earpiece.

In addition the device may also be used for language training. The device can be used when working, resting or sleeping.

Since the mother device has a large/extensive memory capacity, and communicates with the ear devices, it can also be used to transmit other kinds of information to the ear, such as recorded music. Mobile phones connected to the mother device can therefore also be operated through the ear device. Optionally, the mother device can have a built-in radio receiver A micro filter 3 (FIG. 2) is located directly or behind the mouthpiece.

The ear devices are a miniature version of the mother device and are internally identical to it. The keypad and display functions of the main device are emulated by the speaker and microphone components of the ear device. This enables the ear devices to operate and communicate through voice commands.

The ear device or devices can work as a stand-alone device/implant device, wherein another device acts as mother device, for instance a PC or laptop of PDA or the like and performs the same functionality by loading it's program.

FIG. 1C shows the coupling between the sensor network cylinder and data processor unit and its peripheral units.

Figure 21:
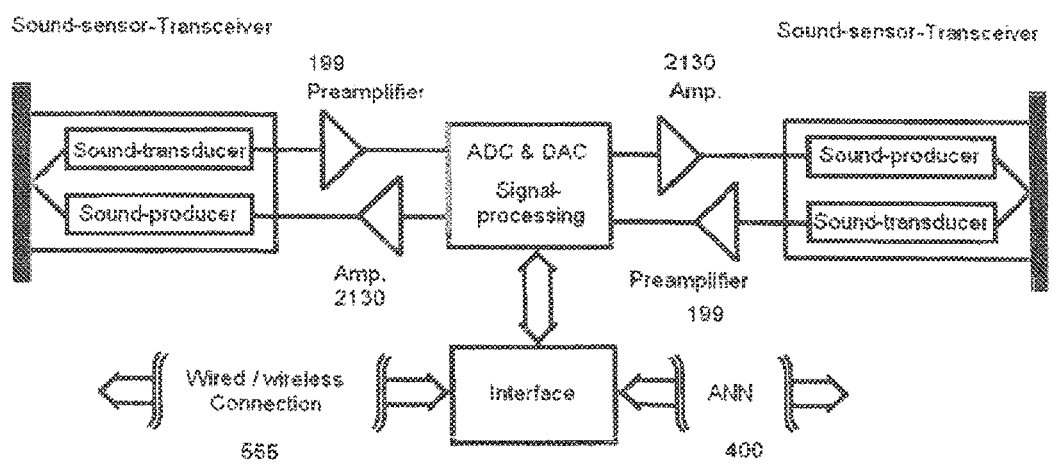
FIG. 21 illustrates a combined sound transducer and sound producer, which act as half-duplex sound units. This principle shows an ear device which can function both ways e.g. both for warning the user and for receiving a signal from outside. Block 555 shows that the ear device can also communicate with a mother device, a PC or the like wirelessly.

Block (199) in FIG. 1C illustrate an amplifier, which is matched to a sensor. These amplifiers are not shown in FIG. 4 for the ear devices. However, the ear devices are miniature equivalents of the main device. The blocks 199 and 2130 in FIG. 21 are used generally throughout the text to indicate an amplifier or preamplifier for different amplification purposes, blocks or sensors. These blocks (199 and 2130) indicate a symbol just for amplification of the particular signal but the technical data of each of these amplifiers are not specified.

The device is capable of allowing a given user access to an automated process for managing a specified health problem, disease, or improving life condition and allowing earlier prevention of disease. These benefits are obtained primarily by storing and analyzing respiratory sound information through the sound sensor network and the Artificial Intelligence data processing.

These could be accessed in the form of data tables and curves and later be used for predicting a user's condition.

Figure 11:
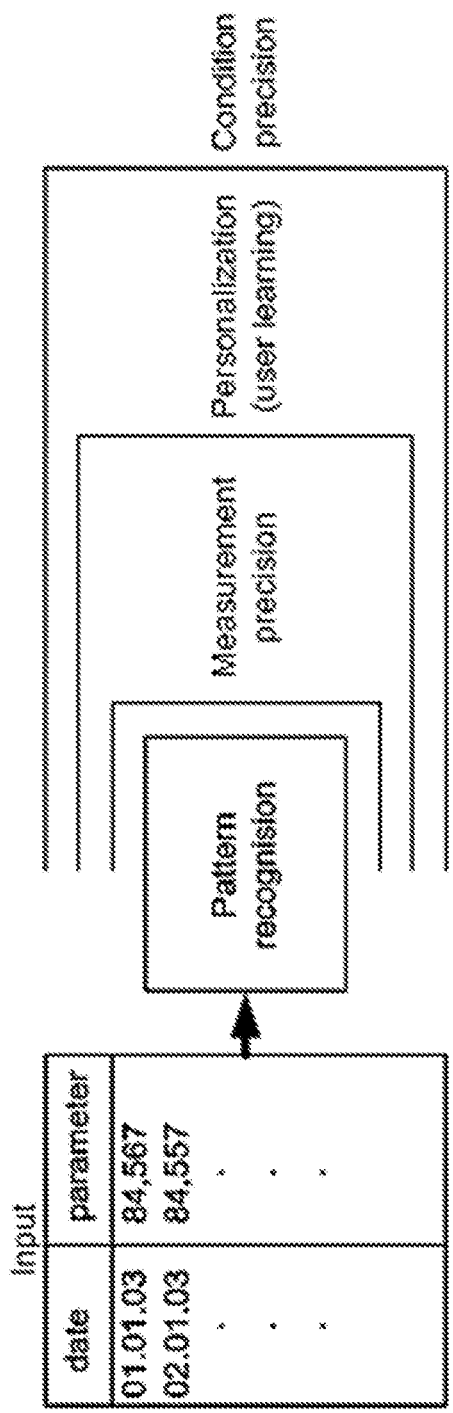
Figure 12:
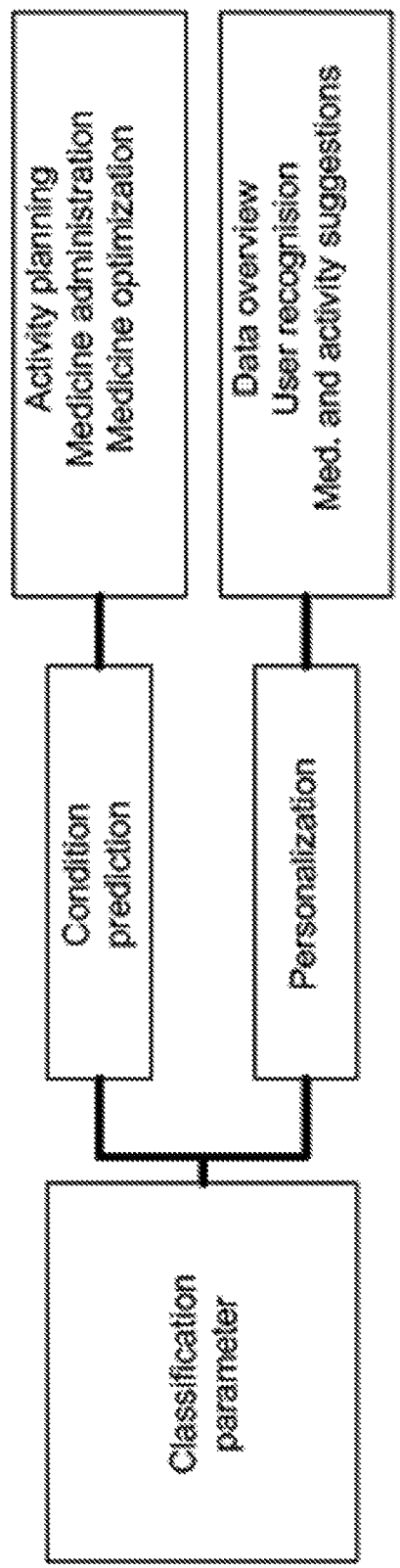
Figure 29:
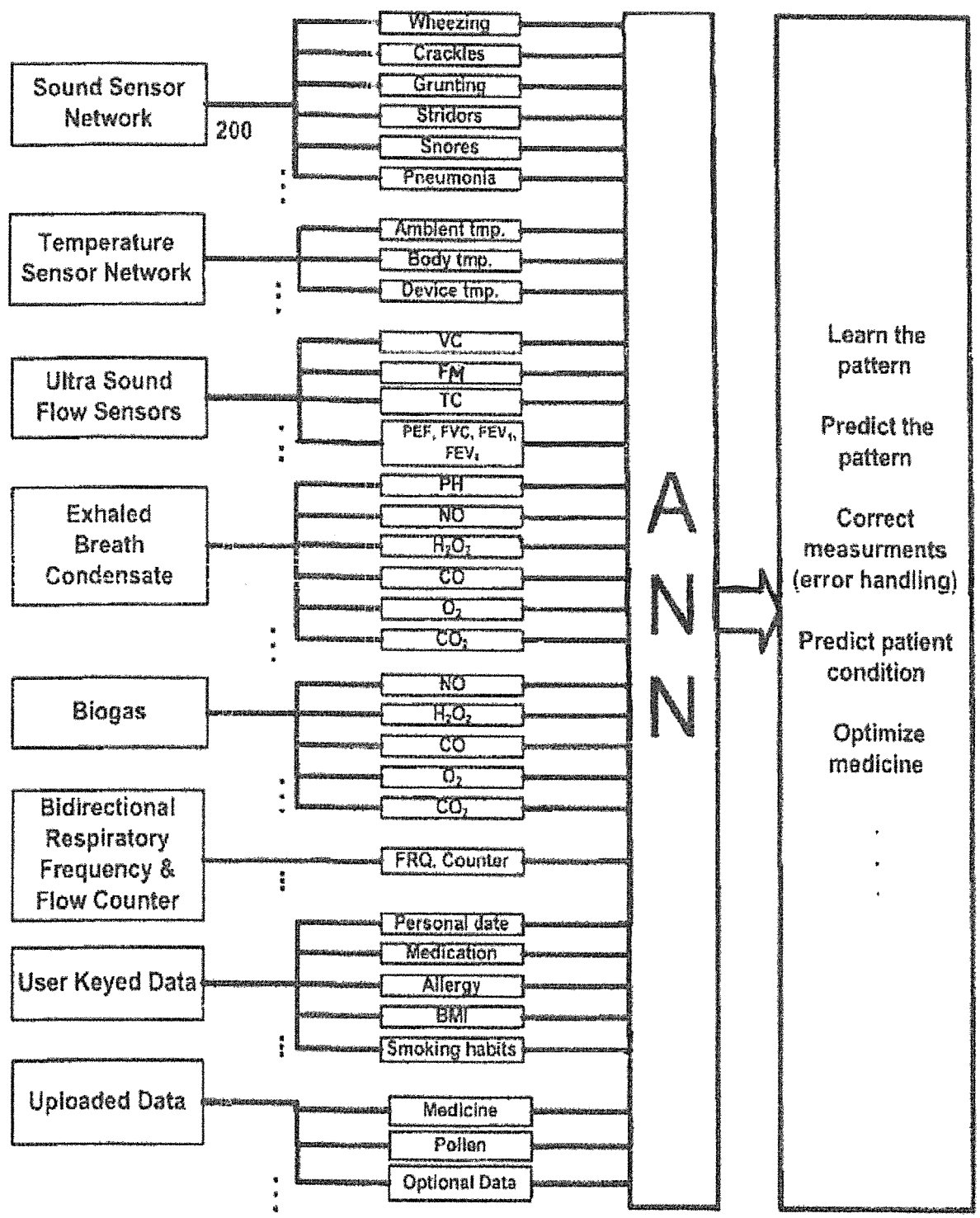
FIG. 29 shows the different groups of the input parameters and data to the artificial neural network and the output of the same network for pattern recognition behavior. This fig. is identical to FIG. 13 but with more details.
Figure 30:
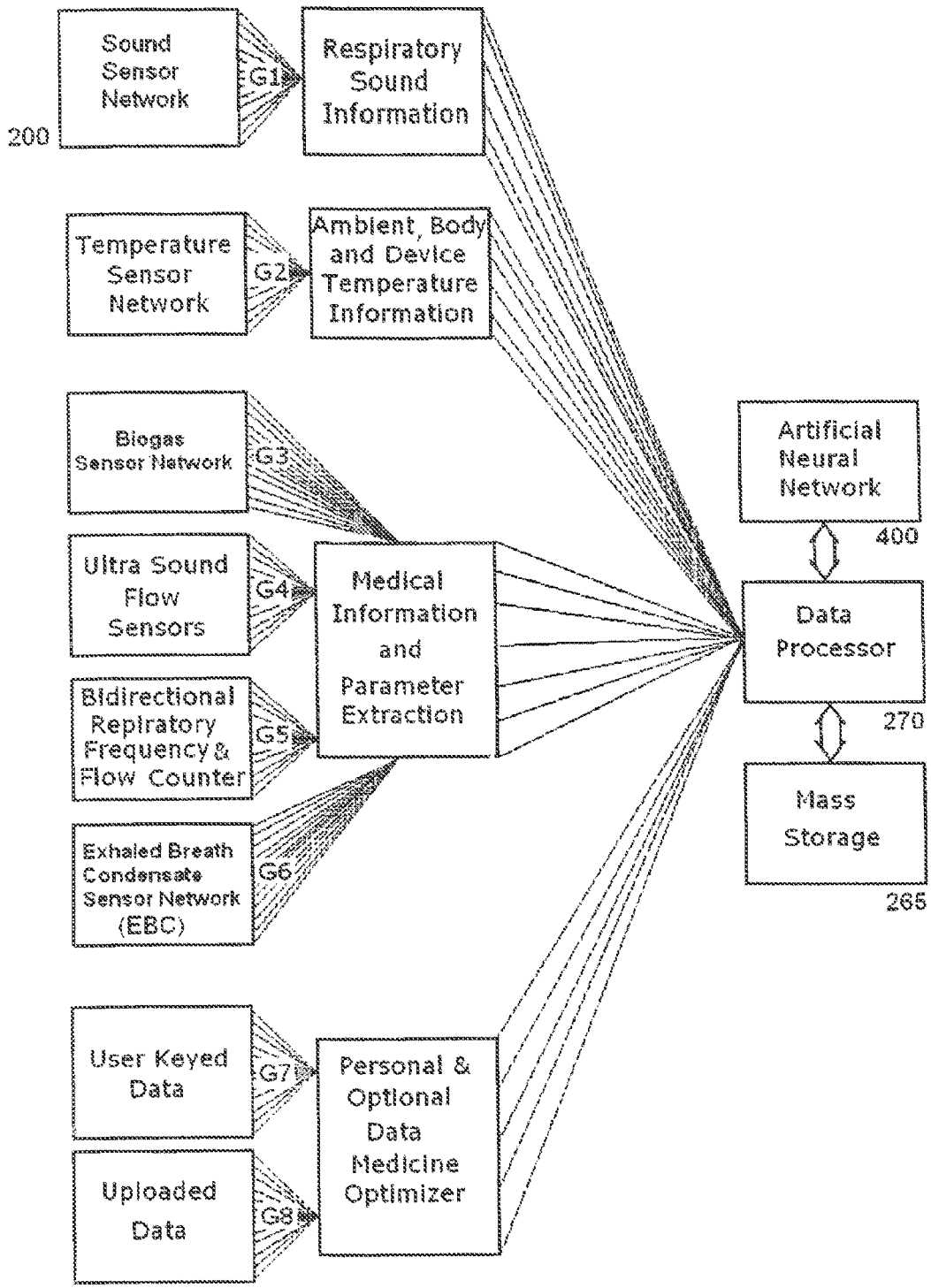
FIG. 30 shows the interconnections of different system blocks. This fig. is identical to FIG. 15 but with more details.

The device manages and advises, but does not perform medical diagnosis without a doctor. However the diagnosis, set by a doctor, could be based on the data collected and analyzed by the device There are 8 groups, G1-G8 (FIGS. 15 and 30) of measurements and stored data input. These data inputs are basic to the learning process of the ANN and its pattern recognition, see FIGS. 13 and 29, and earlier prevention, improved life condition etc. managing health and disease conditions. Those data patterns will have a form of time series (FIGS. 6, 11 and 12).

Figure 3:
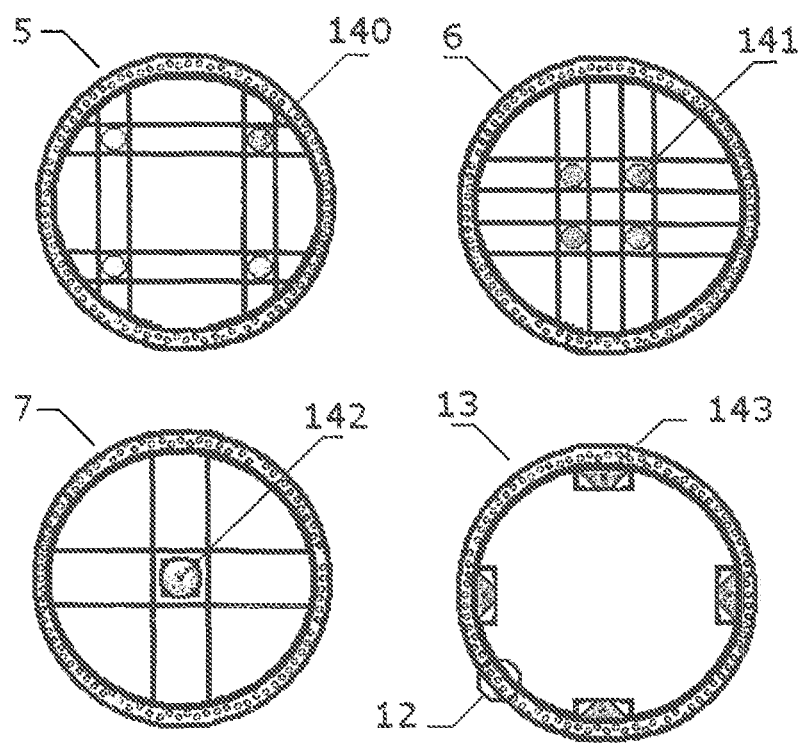

In one embodiment of the invention, the sensor network is placed on the internal sidewalls of the sensor modules inside the device, FIGS. 3 and 14, which forms a three-dimensional array of sensors.

Figure 4:
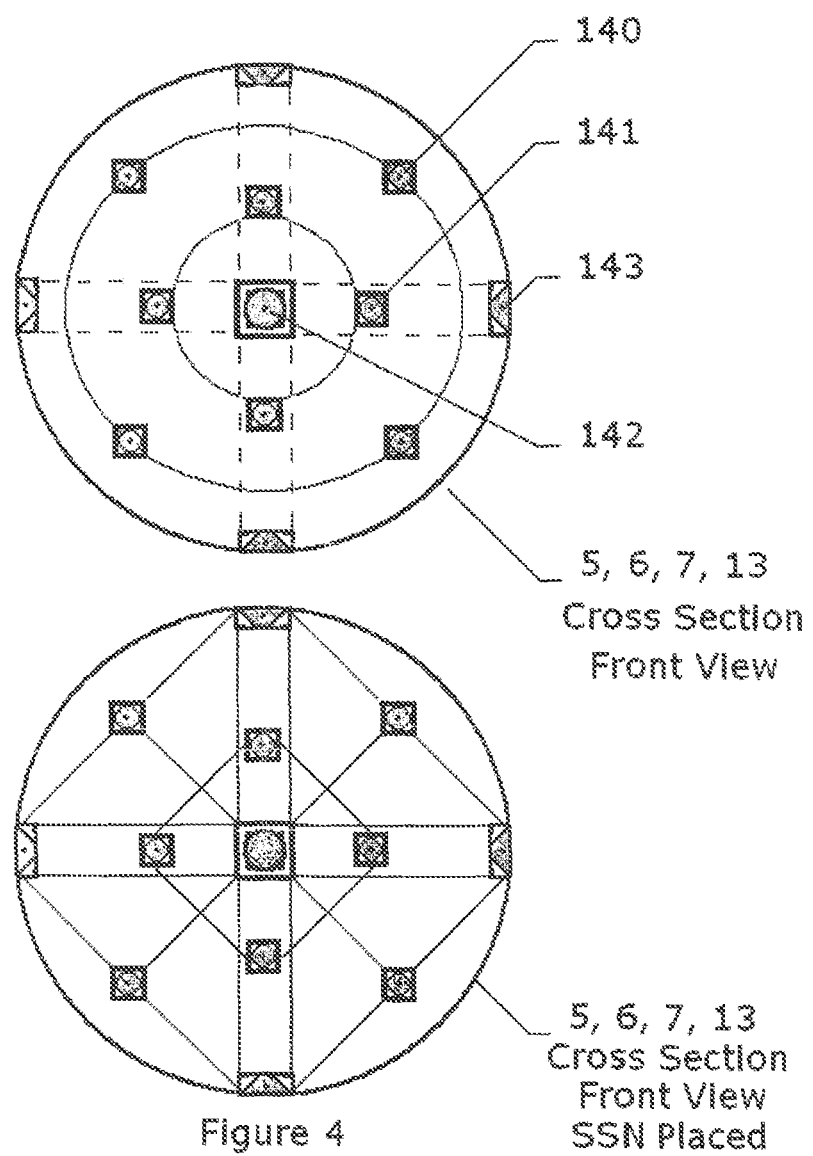

In another embodiment, the sensor network is placed in the middle of the device, forming a net. FIG. 4 shows an example of such a network of sensors. In a third embodiment of the invention, a combination of the first and the second embodiments are used together.

Fabrication examples of biogas- and biochemical sensors, such as NO sensors, include the following sensors, which can, with small modifications, be used: ISO-NOPMC from company WPI, industrial NO-sensor Type I-2S from International Technologies Dr. Gambert GmbH and amiNO-700 or amiNO-100 (size 100 micron) from company Innovative Instruments Inc., or planar sensor array shown in FIG. 23. These three companies also have other types of biochemical/electrochemical sensors such as pH, $H_2O_2$, CO, $O_2$, $CO_2$ etc.

All units are powered by a battery and power supply as showed in FIG. 1B block 500, or implemented by a single SoC solution VLSI-like structure.

Figure 23:
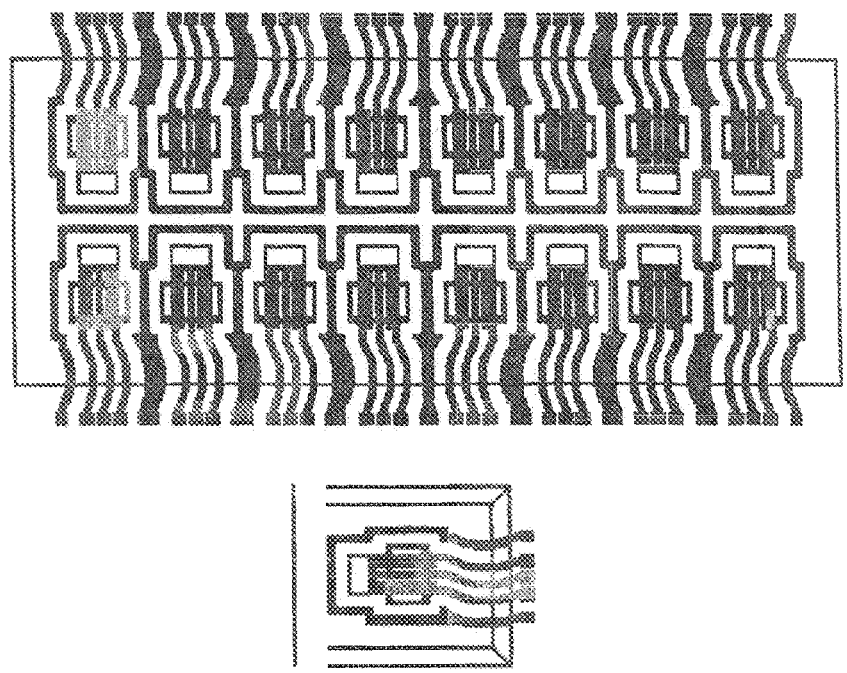
FIG. 23 shows a microchip biogas sensor. It shows also a planar structure opposite of the sensor as shown in FIG. 22.

The ear device or implanted device can be realized like a miniature model of the mother device except for the LCD display and the keypad, for example made of single module system-on-chip (SoC), single ASIC, the micro-sensor network in FIG. 23, a lab on-a-chip as in FIG. 23, memory, sensors network and sound-sensor-transceiver FIG. 21, FIG. 5A block 220. The ear device can be connected or paired to a data processing machine via a wireless or wired link. The ear device can automatically transfer the data to a data processing machine when it is in its socket or in a charging station.

Monitor and key pad (FIG. 1B, blocks 285) interface a data processor (FIG. 1B block 270) through a user interface 280 or through an external computer or the like.

Features/Functionalities:

The mother device and the ear devices may be identical, FIG. 1A. They may therefore include the functionalities, functions and features of the other device. The mother device and the ear devices use the same measurement parameters. The device can be fabricated in such a way that they comprise one or more measurements and functions at the same time, a given relevant combination hereof, a quite new measurement/function and/or all of them included in the application or a combination of them. An ear device or mother device can act as a stand-alone-device, it can be fully functional and it can measure a few parameters.

Snoring Disorder:

The device is directed to two different snoring disorder: inconvenience due to disrupted sleeping and an actual disease.

The mother device and the ear devices may be identical. They may therefore include the functionalities, functions and features of the other device. The mother device and the ear devices use the same parameter measurements. As another example the sound-sensor-network-device can be set up to measure the users snoring during sleep. The device can afterwards digitalize and process received signals representing snoring in a signal-processing-unit. These identified signals can then be recorded or stored in the memory of this device. After a period of use—or by activating its neural network—the device is able to recognize the snore-frequency-components of the user.

After a while all these frequencies are mapped in a pattern-recognition-behavior-unit or a table or in an array.

In the same way, the device can detect other sleep disorders like apnea.

Language Training/Teaching:

The sound sensor network device can also be used for language training/teaching. The language training program, data or file may be uploaded to the mother device in form of MP3 or similar formats. The user has the option to pair the ear device or devices to the mother device during work, recreation or travelling.

Water-Proof:

There are two options/possibilities: the ear devices and the mother device may be water-proof or may not be water-proof.

Measurement of Exhaled NO in Exhaled Breath Condensation and Liquid:

There are at least four different methods of measuring or analyzing the atmospheric gasses or exhaled biogases (for instance NO, $H_2O_2$, $CO_2$, $O_2$ or the like) and the liquid or contents of exhaled condensation. One is to use a mechanical shape or form in the actual tube, e.g. a Gaussian surface (3D), FIG. 20A block 2010, ball-shape, sphere, hemisphere or similar. The Gaussian surface or similar model can be formed in such a way that humidity is collected on the surface, on which it is gathered on the tip in the form of small liquid particles or drops. These Gaussian surfaces can be formed in such a way that humidity is collected on the tip or a certain area of surface. Thus, the device is able to determine the amount of liquid for measurement contents.

Figure 20A:
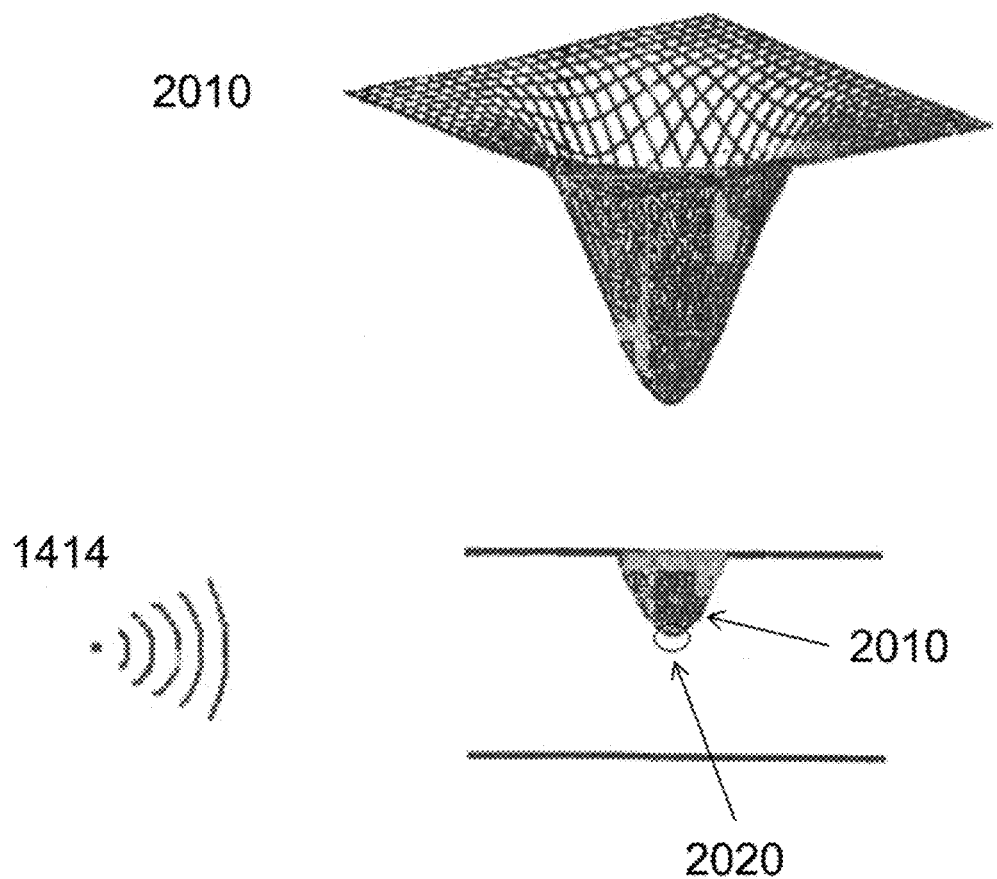
FIG. 20A illustrates a sensor 2020 disposed on a Gaussian surface, block 2010, and placement of the Gaussian surface in the tube in a cross-section view. Block 1414 shows an exhaled breath moisturized gas.
Figure 20B:
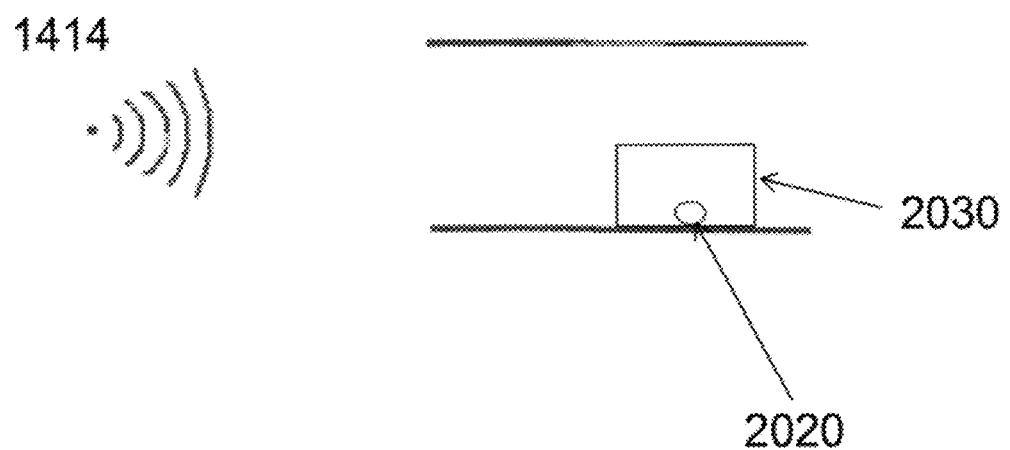
FIG. 20B illustrates a chamber 2030 for collecting condensate in the tube in a cross-section view and a sensor 2020 disposed in the chamber. Block 1414 shows an exhaled breath moisturized gas.

Hereafter the sensors can measure the humidity contents, e.g. NO, $H_2O_2$, pH or the like. The sensors may be positioned on the tip, on the broader surface, or it may have other positions. FIG. 20A block 2010 shows a Gaussian surface and its position in the tube.

Another method is to use a chamber. With regard to the chamber design, the air can circulate in the chamber. Subsequently humidity is collected in the lower part of the chamber. The sensors may be positioned at the lower part of the chamber or may have other positions. These chambers are formed in such a way that humidity easily is collected in a certain area, thus enabling to determine the amount of liquid for measurement of liquids contents.

The third option comprises a moving sensor.

The moving sensors can be formed in such a way that the sensors rotate and collect particle samples. Moving sensors can measure biogas and humidity. Moving sensors comprise sensors network.

Non-moving as well as moving sensors can measure biogas and humidity. Some of these sensors function as reference sensors and some as measurement sensors.

In case of all of the above-mentioned sensors, a microchip, cooler-device, peltier-device or thermoelectric-device (e.g. DT33-401LS from MARLO INDUSTRIES) or similar can be mounted on the surface of the tube, on top of the Gaussian surface, in the lower part of the chamber, to generate liquid from humidity from atmospheric gases or exhaled gases. The sensor can either be positioned close to the chip or can be integrated by annealing, welding, or gluing or similar methods.

The device can measure important fluid parameters in liquid humidity, gasses and plasma, as well as for example in condensated water. These parameters can be measured through a connected external sensor or inside the device. Internal measurements are done by using a microchip or a mechanical item e.g. a Gaussian surface catching the condensated water of the exhaled gas and analyzing its chemical contents by using a sensor. The parameters may consist of NO, $H_2O_2$, CO, pH, or other items, which can be used for diagnosing or monitoring disease, or for other kinds of analysis.

The air flow through the tube can be forced by micromechanicals, MEMS, or a miniature motor with a propeller placed inside or outside the tube or device. This facility, which is placed in- and/or outside the device or tube, can in the same time be used to reach a constant flow through the tube, for making a uniform velocity profile or for producing a certain resistance or pressure of the airflow.

To indicate and measure the total amount of NO produced, both in the nose and in the lungs, the device can be inserted into one or both of the nostrils. The patient has to keep his mouth closed during this process and only exhale through the nose. The device detects both NO produced in the nose and in the lungs.

Afterwards we detect the exhaled breath from the mouth and in this way we are able to compensate the error of the nose-produced NO.

Almost all of the existing biogas and chip sensors that are available in the market for detections and analyzes of exhaled NO-information demand constant humidity and temperature, and some of them even constant flow.

Surface and chamber must be significantly colder than the exhaled gases for condensation to be produced. The changes of the temperature can for example be achieved by a chip.

The Gaussian surface, the chamber and the chip solution must all meet the condition of being much colder than the exhaled gas.

The user exhales into a plastic or a metal tube in the device containing the above-mentioned forms, for example a Gaussian surface. These different items for gathering condensation should be surrounded by cold metal or by a thermal-electric device in such a way that vapor from water or exhalation from the lungs can be developed as condensation.

Normally it takes about ten minutes to get enough condensation, but this process can be shortened by using for example the Gaussian surface.

In some cases the device indicates when enough condensation is gathered for making a measurement. For some sensors a thin layer of steam is enough to be able to measure and analyze exhaled breath condensation.

In one embodiment of this invention it is possible to measure biogases by measuring the condensed form of exhaled gases.

Figure 24:
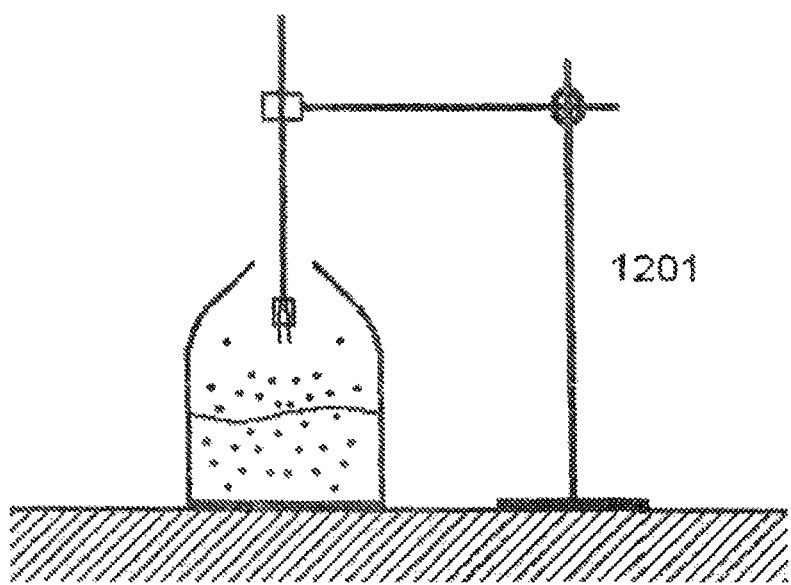
FIG. 24 illustrates the use of the biogas sensor for measurements of gas by mixing exhaled condensate with exhaled breath condensate. Another liquid, distilled water, with enzymes and/or enzymatic solutions, releases biogases, and after that the sensor can measure the contents of the biogases.
Figure 25:
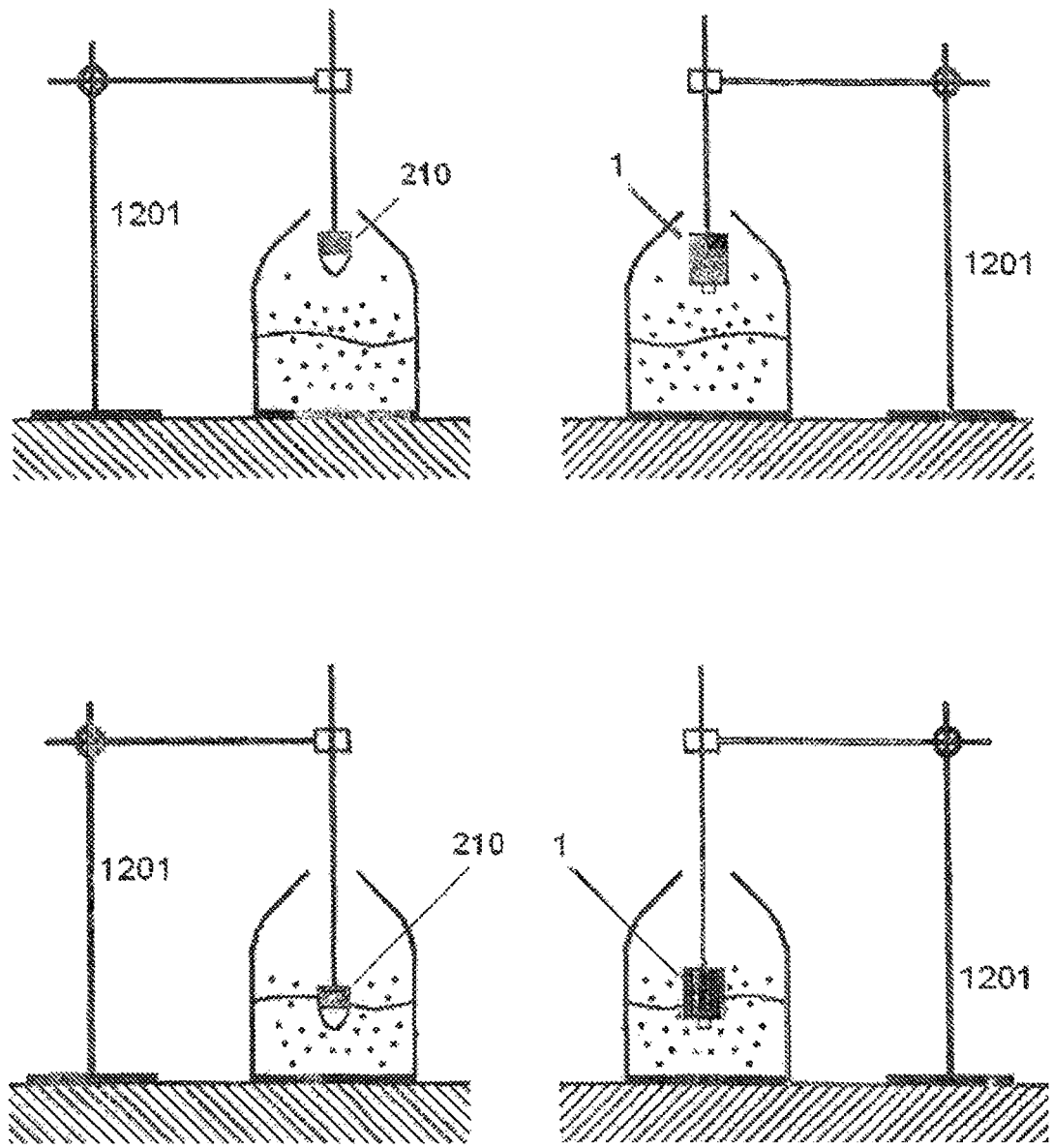
FIG. 25 shows the same principle as in FIG. 24, wherein the mother and the ear device are used for measuring biogases. It also shows that the ear device and the mother device can directly measure liquid components such as pH, dissolved NO and/or other biomarkers.
Figure 26:
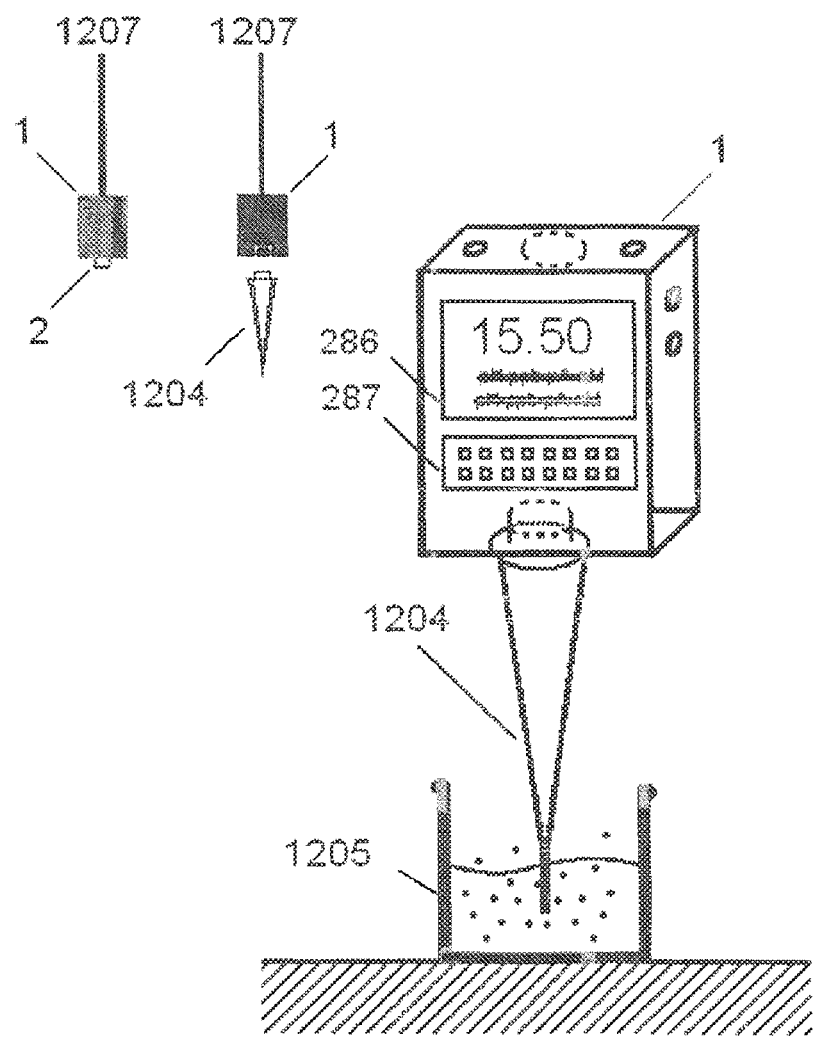
FIG. 26 illustrates how it is possible to remove the mouthpiece of the mother device and to connect a liquid micro sensor.
Figure 27:
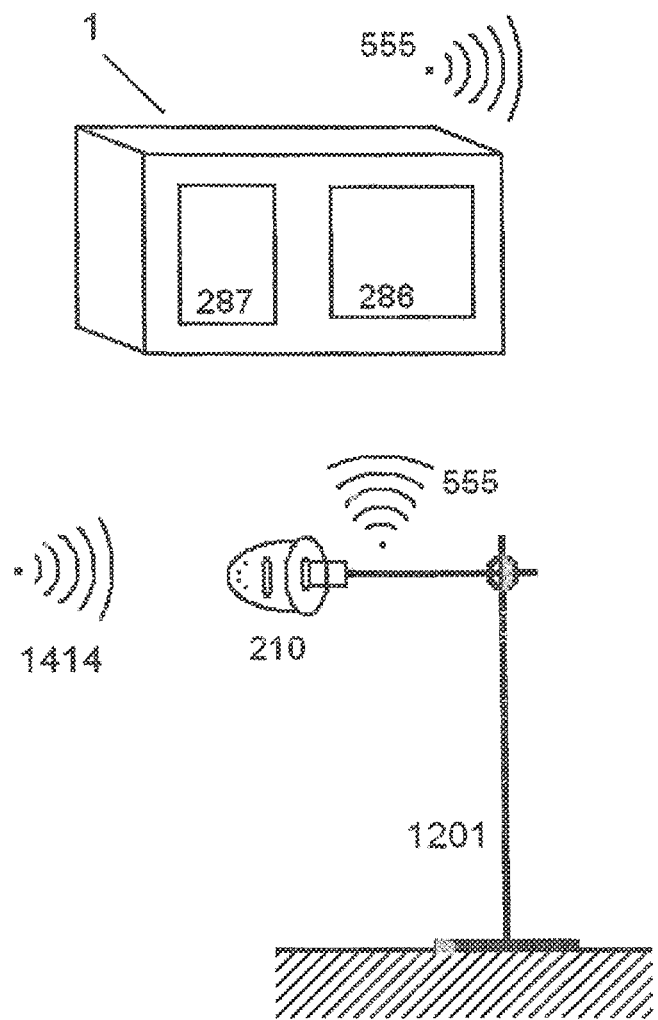
FIG. 27 illustrates how to fasten an ear device to a stand and to collect the sound information signals form the environment and transmitting them to the mother device or to a wirelessly paired terminal.
Figure 28:
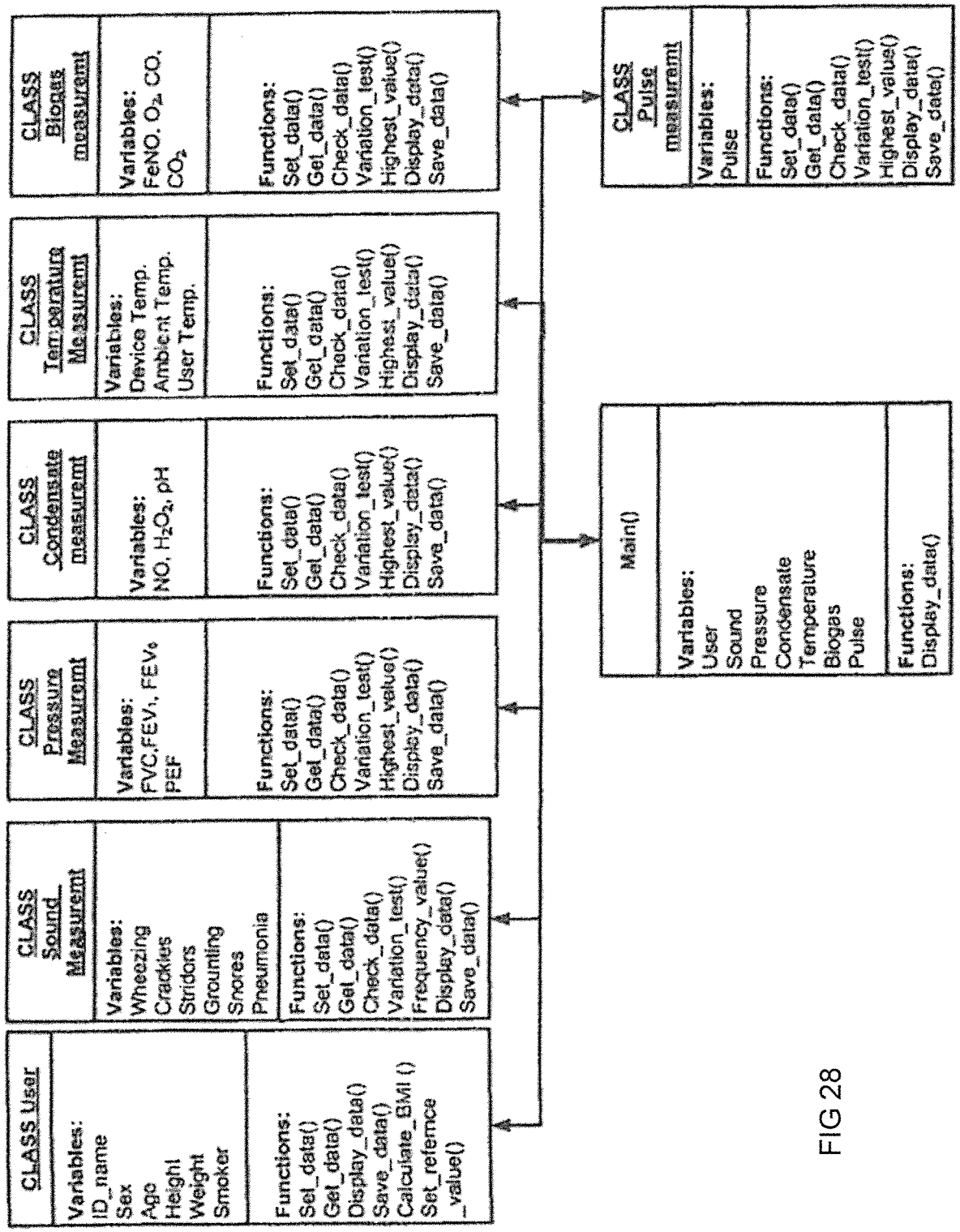
FIG. 28 shows the different classes of the input variables for the neural network. It is identical to FIG. 10 but with more details.

In the performed measurements coherence between Fractional exhaled NO in parts per billion (FePPB) and NO in exhaled breath condensate (EBC) (pA/nM) has been observed. Also a linear relationship between Picoampere (output of the NO sensor) per nanoMolar density (PA/nM) and FePPB of eNO could be demonstrated. Three different tests are performed:

1. Measurements directly on exhaled NO (FIGS. 1A, 1C and 2).
2. Measurements of NO in exhaled breath condensation (FIGS. 24 and 25).
3. Measurements have been made with the addition of enzymatic reagent to a standard buffer solution containing a known concentration of NO (FIGS. 24 and 25). The release of NO from the water solution to gas face could then be demonstrated and reproduced repeatedly with dose dependent signals (FIG. 24). All three tests have been shown to measure the exhaled NO with the accuracy of a few parts per billion. Also, the measurement could distinguish between individuals with varying degree of bronchial inflammation.

These tests were repeated both for persons with healthy lungs and for persons with a high amount of exhaled NO (asthmatic patients). An amount of more than 25 parts per billion or more is considered to detect asthmatic lungs or lungs with bronchial inflammation.

We have as an example tested persons having an amount of between 15 parts per billion (healthy individual) to over 35 parts per billion (asthmatic individual). The microsensor chip (FIG. 23) is a flat realization of the electrode in FIG. 22 these micro-sensors which are unique in the properties of the sensitivity and selectivity of the sensor surface or sensor tip.

Figure 22:
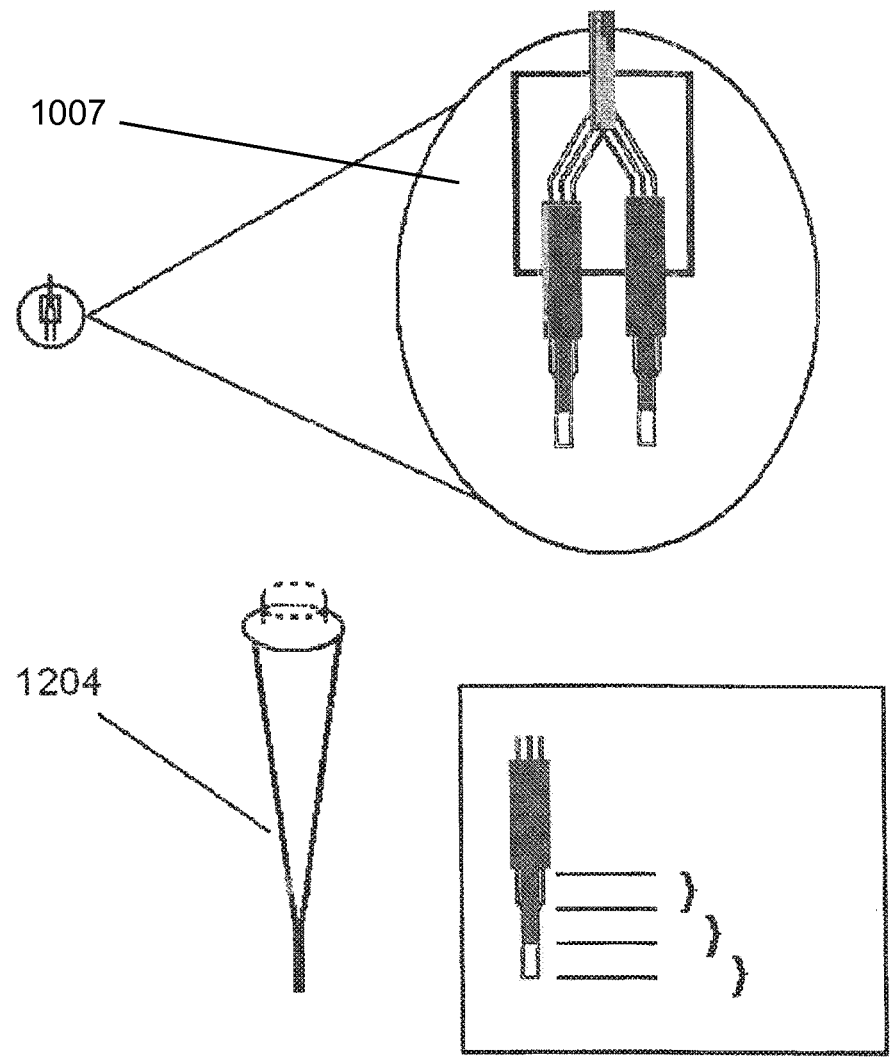
FIG. 22 shows a biogas sensor (BS) that measures NO. Module 1007 shows a double sensor. Module 1204 shows the application of such a double sensor. Module 1204 can be connected to the mother device for measuring liquid and condensate (see FIG. 26).

Those sensitivities are achievable party by the silver material of the electrode or planer and by the positive resting potential of 18 mV-850 mV. Also, the small distance between the sensor tip and reference electrode is an important to diminish noise from other intervening molecules. The selectivity is achieved by having semi permeable properties of the sheeting membrane that effectively exclude other molecules from diffusing into the covered sensor tip, allows almost only NO to pass. By using the same principle with other materials and sheeting membranes it is possible to make other sensors that select different liquids or gases. FIGS. 22 and 23 show two different examples.

Figure 17:
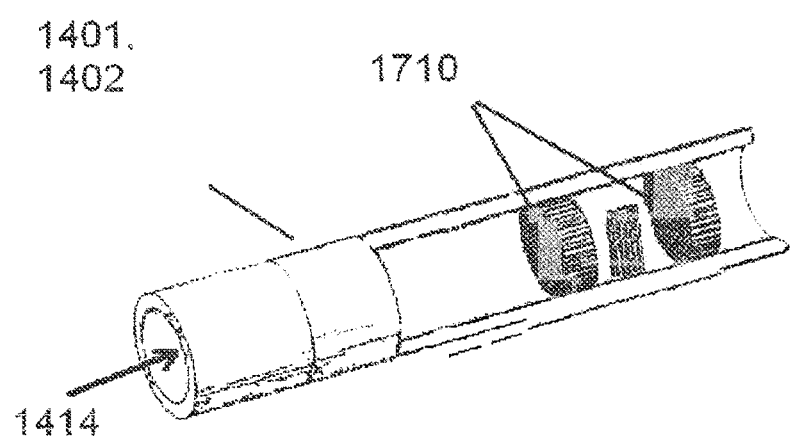
FIG. 17 shows an embodiment of the presently disclosed device with two discs placed inside the mouth piece to achieve a uniform velocity profile. The blocks 1710 show the discs comprising small longitude pipes.
Figure 18:
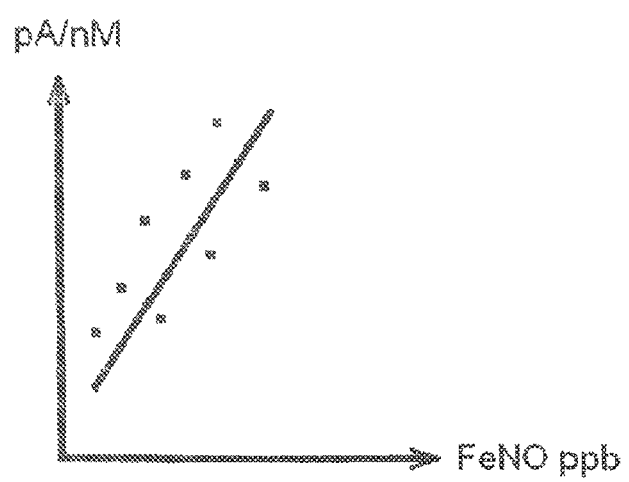
FIG. 18. shows the sensor output signal as a function of NO density.
Figure 19:
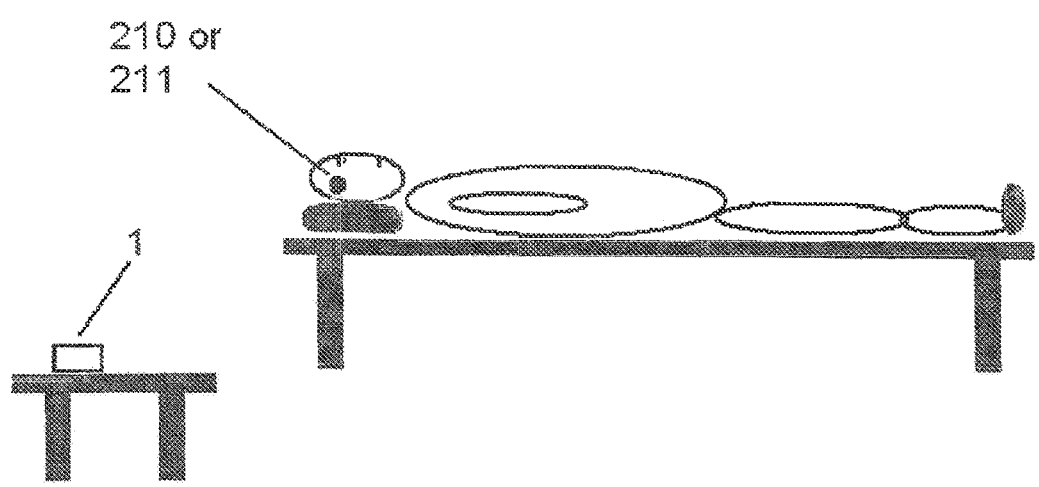
FIG. 19 shows a user wearing an ear device and the mother device placed adjacent to the bed. This principle is used for supervision, snore-detection, apnea-detection or for learning.

By placing one or more discs (FIG. 17, blocks 1710), which can also be used to form a uniform velocity profile or to create resistance and pressure when blowing in the device.

The smaller the pipes are throughout the disc, the more resistance and pressure is produced. The discs comprise a few or several pipes. The pipes may be of different or same form and size. They may be round, circular, 2D, 3D or any form of elongated/oblong form and the like.

By placing a disc of pipes (FIG. 17) in the mother device a constant flow is achieved, and by using exhaled condensate a constant humidity can be achieved in the tube. This demands a position of the one or more valves (not shown in FIG. 17) after the mouthpiece but before the position of the sensors. When the user inhales through the mouthpiece, the valves open, and let the air pass through. When the user exhales, the valves close and the air passes through the mouthpiece and then through the mother-device and is passed away through flow exit-port (shown in FIG. 1A and FIG. 2). The opening and closing of the valves are not activated by certain measurements, like bidirectional flow measurements.

Additional Functionality:

The device can have preinstalled or preloaded certain/particular software to perform and fulfill a few or more functions for a short or a long period, for instance for 2 or 3 weeks, or for one year or for several years. As an example a 2 or 3 weeks program can simply consist of a measure program for detecting user PEF-blow.

For one or several years data treatments and measurements, for example ageing of the lungs can be measured with the time dependence factor or evolution of environmental effect such as pollen, humidity and other environmental effects on the body or lungs ("user conditions"), can be measured and stored.

Therefore the device and its method and system can act as a simple machine or as a very complicated machine depending of which program the doctor chooses.

To detect snoring and help the users of the device, the snore-detecting device structure can be fabricated simply without the artificial neural network or a simple linear ANN. By simply loading the users snore data or using a software module to map the snore-frequency in the memory and use it as a reference avoid use of ANN.

There is a difference between the frequency and the acoustic of different users. This makes the device cheaper to produce since the expense of adding an artificial neural-network is saved.

By using this machine the device can indicate and display a warning for the user based on the user's condition. The indicator or the alarm can be realized or implemented as an alarm signal having a particular sound, speech, light or as a beep sound of a particular frequency.

This alarm signal can warn the user by waking him/her up or by making him/her conscious that he/she should change his/her position. The user can be taught to change their position for example from a back position to a side position. The user may wear one or both ear-devices and the mother-device may be placed on for example a table at the bedside. The three devices all together watch and analyze the frequencies—either the ear device or the mother device can produce the alarm signal to make the user turn to another position in bed.

In severe cases, for example if the user because of an illness is not able to breathe or the user has been drinking alcohol, the device may alarm to make the user turn to another position and the alarm-signal can also be enforced.

The same principle is used as an example for an asthma patient and the device can again warn them before the asthmatic attack occurs.

An early warning before an asthmatic attack or before a similar condition can be sent by the device to warn the user to take their medicine or advice some other kind of action depending on the degree of the condition.

The ear device or mother device can similarly be programmed to recognize a given condition from the subject/the machine/device or the like. As an example the ear device or system can be programmed to indicate or monitor a particular sound or vibration. In this case the ear device can transmit this information to the mother device or to the controlling system or the like for the indication of an error, for a disorder or the like or in the same way for acceptance and improvement of the condition (production service).

Detection of Vibration and Pulse:

The ear device can measure and collect both vibrations and sound signals and since the heartbeat and heart vibrations are far lower than the sound of the lungs, the device is able to detect both lung sounds and heart rate and analyze to indicate the user's condition. By putting the ear device(s) on the artery of the wrist, on the heart or on the artery of the neck it is also possible to measure heart-signals and pulse FIG. 5B.

Connection of the Mother and/or Ear Device to Hospital Equipment:

It is possible to use the mouthpiece of the mother device as a link between the mouth of the patient/or a mask and hospital equipment (such as respirator) to provide the hospital equipment with more parameters and detailed analysis, supervision, alarm for a given condition and data processing and the like.

Combination of Sensor Networks:

In order to limit the number of devices required by e.g. a person using lung support/assistance, impaired hearing etc. The sound sensor network device can also function as a cell phone and/or hearing aid.

It can be added to "the section about loudspeakers and microphones in ear devices" that:

When a person suffers from impaired hearing, such person can activate an option in the sound sensor network device, which means that one or more of the sound sensors is activated to capture external sound and reproduce the sound by a speaker. The sensors can be adapted to meet the requirements of the user in question. The ear device can be paired to the mother device and can be set up to receive environmental sound information signals to enhance the signals and prepare them to reproduce those signals to meet the requirements of the impaired hearing of the user in question. The mother device may be placed close to the sound information source signal to transmit the information to the ear device wirelessly and reproduce it to the user as shown in FIGS. 1A and 5A.

A simple manufacturing method could be described as follows. The Sound Sensor Network is a network of sound micro sensors, a network of micromechanical sound sensors and/or MEMS, a network of sound transducers, a network of semiconductor sound micro sensors or microchips, or the sound micro sensors manufactured using semiconductor material on the same substrate or silicon on insulation (SOI) like substrate. Sound micro sensors can be built up through Micro- or Nanotechnology based semiconductor or other similar material. The Sound Sensor Network is placed on the internal sidewall of the device (FIG. 2 143). FIG. 2 also shows a 30 row of membranes/diaphragm (5, 6 and 7). These membranes/diaphragm 5, 6, 7 are built by net formed in such a way that air and sound can pass through the cylinder tube without any undesirable blocking of airflow or sound. which can cause turbulence, reflection or distortion of such signal information. Similar embodiments are shown in FIGS. 8 and 14A and B.

The output or response of the Sound Sensor Network to the system includes noise that is caused by turbulence between the airflow and the sound micro sensors 143. An algorithm and/or calculation will take this noise into account and eliminate it, for example by letting the system understand it as a common mode signal or/and sound noise in comparison to a differential signal information.

Similarly, if the output or response of the Sound Sensor Network to the system includes noise caused by turbulence between the airflow and the sound micro sensors 5, 6, 7 (chain of micro sensors on membranes or diaphragm or net 5, 6, 7), an algorithm and/or calculation will take the noise into account and eliminate it, for example by letting the system understand it as common mode signal or/and sound noises. These turbulent effects can also be eliminated by using flat micro sensors combined with a cylindrical or cone formed elongated/oblong tube as shown in FIGS. 14A and B, which is an alternative to FIG. 2.

The device can communicate with the user through a display and key pad (FIGS. 1A and 1B). The display is a monitor such as an LCD and the like, which is placed on the device as shown in FIG. 1A. Alternatively the device can be connected to a laptop or PC like screen through a wired or a wireless connection.

Similarly, the key pad 285 is a simple keyboard or a few buttons placed on the device. Alternatively, the device be connected to a laptop or PC like keyboard.

The acquired or collected data from analog micro sensors will be digitalized using an analog to digital conversion by a given discrete Integrated Circuit (IC). Subsequently, using a microprocessor 270 such as Intel StrongARM SA-1100 or Intel XScale PXA255 or other data processor from Intel® Corporation or Athlon™ Corporation or the like, the signals can be analyzed in their time domain and/or frequency spectrum by using for example Discrete Fourier Transformation, Fast Fourier Transformation (FFT) or other similar algorithm. Throughout this document, these techniques and algorithms are referred to as Fast Fourier Transformation (FFT).

Components for the external memory 260, 261 and 265 communicate with the microprocessor 270 through a databus 262, or separately with the data processor. The chosen microprocessors have an integrated databus controller.

A choice for the RAM module 260 could be Intel 28F128J3, Intel 28F128K3 or the like. The ROM module could be Atmel 28LV010 or the like. The mass storage module could be compact flash card from Dane-elec DA-CF-1024 or disc drive as Seagate St380011A and the like. Intel Xscale PXA255 has Bluetooth™ and USB modules, which could be used as wireless and wired communication 510. All units are powered up by battery power supply 500. Monitor and key pad 285 interface the microprocessor 270 through a user interface 280 or through an external computer or the like.

The data collected from SSN or data microsensors network needs to be transformed into the frequency domain through for example 512 point FFTs, 1024 point FFTs, 2048 point FFTs or the like. A simple solution is to make phase shifts for the FFT results and sum them in a frequency domain beam former to calculate signal energies. Afterwards the magnitude of signal energies can be calculated. These data will be recorded in the memory.

The Flow Meter (FM) can be implemented by using an ultrasound principle in a cylindrical flow meter, which is known as Capacitive Micromachined Ultrasonic Transducers or cMUT Technology. This method offers very accurate measurements.

Figure 10:
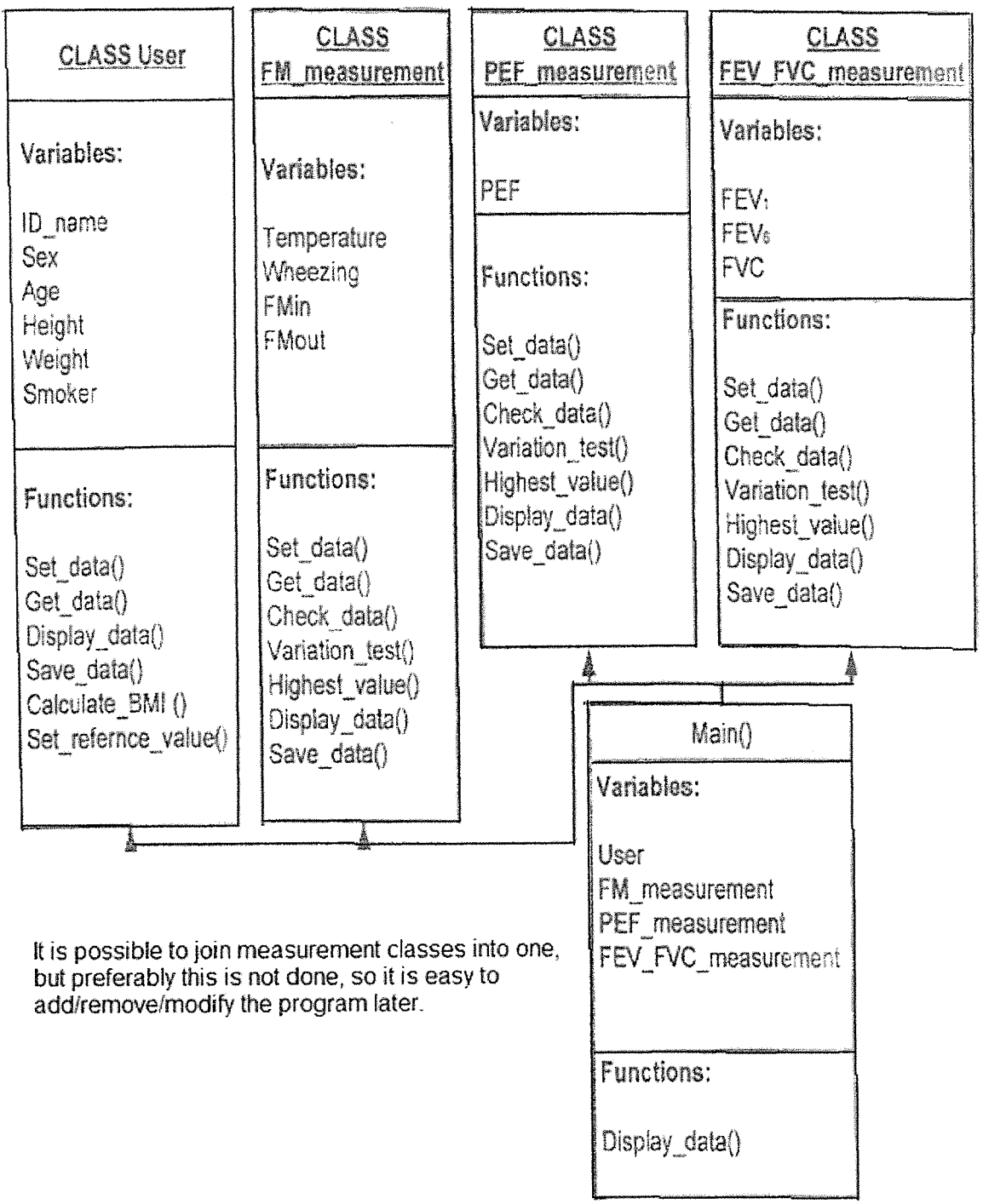

FIG. 10 illustrates a possible idea to software in the device. It has only an illustrative purpose and should be used only as an example of a possible implementation.

The design should be object-oriented. There are no comments to variables and functions because they are simple and—will certainly be modified and updated in the process of real implementation. By "real implementation" is meant a process of the real software development.

Artificial Neural Network (ANN) commercial fixed package example:

One of the following mentioned simulator environments and their ANN package solution, other similar products or a combination of them can be applied to development and implementation of the ANN in the device and for its use:

1—BrainMaker
   Name: BrainMaker, BrainMaker Pro
   Company: California Scientific Software
   Address: 10024 Newtown rd, Nevada City,
   CA, 95959 USA
2—SAS Enterprise Miner Software
   Name: SAS Enterprise Miner Software
   Company: SAS Institute, Inc.
   Address: SAS Campus Drive
   Cary, N.C. 27513
   USA
3—NeuralWorks
   Name: NeuralWorks Professional II Plus (from NeuralWare)
   Company: NeuraiWare Inc.
   Address: RIDC Park West
   202 Park West Drive
   Pittsburgh, Pa. 15275
4—MATLAB Neural Network Toolbox
   The Mathworks Inc.
   3 Apple Hill Drive
   Natck, Mass. 01760
5—Propagator
   Contact: ARD Corporation,
   9151 Rumsey Road,
   Columbia, Md. 21045,
   USA
6—NeuroForecaster
   Contact: Accel Infotech (S)
   Pte Ltd; 648 Geylang Road;
   Republic of Singapore 1438;
7—Products of NESTOR, Inc.
   530 Fifth Avenue;
   New York, N.Y. 10036;
   USA;
8—Ward Systems Group (NeuroShell, etc.)
   Ward Systems Group, Inc.
   Address: Executive Park West
   5 Hillcrest Drive
   Frederick, Md. 21702
   USA
9—Neuralyst
   Company: Cheshire Engineering Corporation;
   Address: 650 Sierra Madre Villa, Suite 201,
   Pasadena Calif. 91107;
10—NeuFuz4
   2900 Semiconductor Drive
   Santa Clara, Calif., 95052
   USA

The invention claimed is:

1. A device for obtaining a parameter for nitric oxide (NO) in exhaled air, said device comprising:
a housing defining a conduit having an inlet and an outlet, said conduit comprising a Gaussian surface for collecting condensate from the exhaled air, the Gaussian surface formed such that condensate is collected on the Gaussian surface, the conduit further comprising a thermo-electric device arranged for cooling the conduit to generate the condensate from the exhaled air, the conduit further comprising a sensor, said sensor being disposed on the Gaussian surface, said sensor for determining said parameter in the condensate on the Gaussian surface and for generating an electrical signal representing said parameter based on airflow generated by a person blowing in said conduit at said inlet such that the airflow contacts the Gaussian surface and forms the condensate, said sensor having an electrical output for outputting said electrical signal,
an analog-to-digital converter having a converter input and a converter output, said converter input being electrically connected to said electrical output of said sensor such that the electrical signal is converted to a digital signal by the analog-to-digital converter, and
a processor having a first digital input and a second digital input and a first digital output, said first digital input of said processor being electrically connected to said converter output for receiving said digital signal,
wherein said sensor is a NO sensor capable of measuring NO in condensate of exhaled air.

2. The device according to claim 1, further comprising a memory unit having a digital input and a digital output, said digital output of said memory unit connected to said second digital input of said processor for transmitting previously stored reference values identified in a hierarchy.

3. The device according to claim 2, wherein said processor establishing on a basis of said reference values and on a basis of values derived from said digital signal received from said analog-to-digital converter, a health state of said person and presenting information relating to said health state to said person and storing said health state in said hierarchy.

4. The device according to claim 1, wherein said device further comprises a transceiver for transmitting and receiving data representing physiological information determined by external units.

5. The device according to claim 1, further comprising at least one sound sensor.

6. The device according to claim 1, wherein said at least one sound sensor measures ultra sound.

7. The device according to claim 1, further comprising at least one of a temperature sensor, an air pressure sensor, and a moisture sensor.

8. The device according to claim 1, further comprising a sensor for measuring a second parameter selected from the group consisting of: pH, $H_2O_2$, CO, $O_2$, and $CO_2$ in condensate of exhaled air.

9. A method for obtaining a physiological parameter regarding an individual using a device comprising:
providing a housing defining a conduit having an inlet and an outlet, said conduit comprising a Gaussian surface that is arranged to collect condensate from exhaled air on a tip of the Gaussian surface,
providing at least one sensor capable of measuring nitric oxide (NO) in said condensate of exhaled air for determining said physiological parameter;
mounting said sensor at the tip of the Gaussian surface;
providing a thermo-electric device disposed in the conduit such that the thermo-electric device cools the Gaussian surface;
cooling the Gaussian surface, thereby generating condensate from the exhaled air;
collecting the condensate from exhaled air on the at least one sensor;
generating an electrical sensor signal representing NO in said condensate;
outputting the electrical sensor signal from said sensor,
converting the electrical sensor signal to a digital signal;
receiving said digital signal at a first digital input of a processor.

10. A device for obtaining a parameter for nitric oxide (NO) in exhaled air, the device comprising:
a housing defining a conduit having an inlet fluidly coupled to an outlet, the conduit comprising:
a Gaussian surface formed on an internal wall of the conduit between the inlet and the outlet,
a thermo-electric device, and
an NO sensor comprising an electrical output, the NO sensor disposed on the Gaussian surface such that the exhaled air is cooled by the thermo-electric device, forming condensate on the Gaussian surface and collecting at the NO sensor, which causes the NO sensor to generate an electrical signal that corresponds to the parameter and output the electrical signal via the electrical output;
an analog-to-digital converter having a converter input and a converter output, the converter input being electrically coupled to the electrical output of the NO sensor such that the electrical signal is received from the NO sensor and converted to a digital signal;
a processor electrically coupled to the converter output of the analog-to-digital converter; and
a non-transitory, processor-readable storage medium communicatively coupled to the processor, the non-transitory, processor-readable storage medium comprising one or more programming instructions thereon that, when executed, cause the processor to:
receive the digital signal,
determine the parameter from the digital signal, and
generate data corresponding to the parameter.

11. The device of claim 10, further comprising at least one of a temperature sensor, an air pressure sensor, and a moisture sensor.

12. The device of claim 10, further comprising a second sensor for measuring a second parameter selected from the group consisting of: pH, $H_2O_2$, CO, $O_2$, and $CO_2$ in condensate of exhaled air.

13. The device of claim 10, wherein:
the Gaussian surface comprises a tip; and
the NO sensor is disposed on the tip of the Gaussian surface.

14. The device of claim 10, wherein the non-transitory, processor-readable storage medium further comprises one or more additional programming instructions thereon that, when executed, cause the processor to display the data on a display in wired or wireless communication with the processor.

15. The device of claim 14, wherein the display is a mobile phone display.

* * * * *